United States Patent [19]

Rivero et al.

[11] Patent Number: 5,554,625
[45] Date of Patent: Sep. 10, 1996

[54] SUBSTITUTED BIPHENYLMETHYLIMIDAZOPYRIDINES

[75] Inventors: Ralph A. Rivero, Tinton Falls; Prasun K. Chakravarty, Edison; William J. Greenlee, Teaneck; Nancy J. Kevin, Clifton; Nathan B. Mantlo, Westfield, all of N.J.

[73] Assignee: Merck & Co., Inc., Rahway, N.J.

[21] Appl. No.: 416,790

[22] PCT Filed: Jul. 7, 1993

[86] PCT No.: PCT/US93/06407

§ 371 Date: Jan. 6, 1995

§ 102(e) Date: Jan. 6, 1995

[87] PCT Pub. No.: WO94/02142

PCT Pub. Date: Feb. 3, 1994

Related U.S. Application Data

[63] Continuation of Ser. No. 916,303, Jul. 17, 1992, abandoned.

[51] Int. Cl.⁶ .................. A61K 31/435; C07D 471/04
[52] U.S. Cl. .................. 514/303; 514/234.2; 544/127; 546/118
[58] Field of Search .................. 546/118; 514/303, 514/234.2; 544/127

[56] References Cited

U.S. PATENT DOCUMENTS

| | | | |
|---|---|---|---|
| 5,102,880 | 4/1992 | Chakravarty et al. | 546/118 |
| 5,128,327 | 7/1992 | Chakravarty et al. | 546/118 |
| 5,223,499 | 6/1993 | Greenlee et al. | 546/118 |
| 5,332,744 | 7/1994 | Chakravarty et al. | 546/23 |

FOREIGN PATENT DOCUMENTS

| | | |
|---|---|---|
| 0260613 | 3/1988 | European Pat. Off. |
| 0399731 | 11/1990 | European Pat. Off. |
| 0400974 | 12/1990 | European Pat. Off. |
| 0420237 | 4/1991 | European Pat. Off. |
| 0426021 | 5/1991 | European Pat. Off. |
| 0434038 | 6/1991 | European Pat. Off. |

Primary Examiner—Bernard Dentz
Attorney, Agent, or Firm—Valerie J. Camara; Mark R. Daniel

[57] ABSTRACT

Biphenylmethylimidazopyridines of the structure (I) are angiotensin (II) antagonists and therefore useful in the treatment of hypertension and related cardiovascular disorders and ocular hypertension.

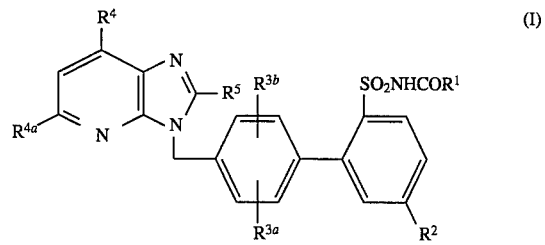

9 Claims, No Drawings

SUBSTITUTED BIPHENYLMETHYLIMIDAZOPYRIDINES

This application is a 371 of PCT/US93/06407 filed Jul. 7,1993 which is a Continuation of Ser. No. 07/916,303 filed Jul. 17, 1992 and now abandoned.

SUMMARY OF THE INVENTION

This invention is concerned with novel compounds of general structure I:

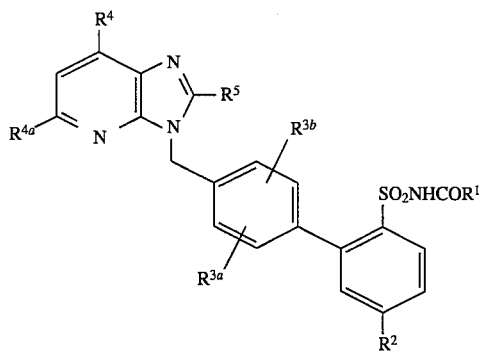

wherein $R^2$ is a non-functional substituent such as alkyl, alkoxy, or aryl which are angiotensin II (AII) antagonists demonstrating balanced $AT_1/AT_2$ activity thus useful in the treatment of hypertension and related cardiovascular disorders and in ocular hypertension.

This invention is also concerned with novel pharmaceutical formulations with one of the novel compounds as active ingredients and the method of treating hypertension and related cardiovascular disorders or ocular hypertension with a novel compound or pharmaceutical formulation thereof.

The invention is also concerned with novel processes for preparing the novel compounds.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (A II) is an octapeptide hormone produced mainly in the blood during the cleavage of angiotensin I by angiotensin converting enzyme (ACE) localized on the endothelium of blood vessels of lung, kidney, and many other organs. It is the end product of the reninangiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. Clin. Exp. Hypertens. A4, 27–46 (1982); D. H. P. Streeten and G. H. Anderson, Jr.—*Handbook of Hypertension, Clinics Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 399,731 and 400974 disclose imidazopyridines similar to those described herein which are also A-II antagonist.

DETAILED DESCRIPTION OF THE INVENTION

The novel compounds of this invention have structural formula I:

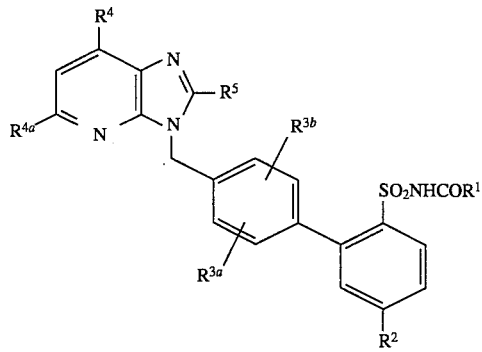

or a pharmaceutically acceptable salt thereof;
wherein:
$R^1$ is
, a) $C_{1-6}$ alkyl,
b) $C_{1-6}$ alkylamino,
c) $C_{1-6}$ alkoxy-$(CH_2)_n$—, wherein n is 1 or 2,
d) aryl-$(CH_2)_S$—, wherein S is 0 to 3
e) $C_{1-6}$ alkylthio-$(CH_2)_n$—,
f) aryl, either unsubstituted or substituted with
  1) $C_{1-6}$ alkyl,
  2) aryloxy,
  3) $C_{1-6}$ alkoxy,
  4) —Cl,
  5) —Br, or
  6) $C_{1-6}$ alkylamino;
$R^2$ is
a) —Cl,
b) $C_{1-6}$ alkyl,
c) $C_{1-5}$ alkoxy,
d) $C_{1-5}$ alkoxy-$CH_2$—,
e) di($C_{1-5}$ alkyl)amino-$CH_2$—,
f) pyrrolidin-1-yl-$CH_2$—,
g) morpholin-1-yl-$CH_2$—,
h) polyfluoro-$C_{1-5}$ alkoxy,
i) aryl,
j) $C_{1-5}$ alkyl-S-(O)S-$(CH_2)_S$— or
k) aryl-$(CH_2)_n$—;
$R^{3a}$ and $R^{3b}$ are independently
a) H,
b) F, Cl, Br or I,
c) $C_{1-4}$ alkyl,
d) $C_{1-4}$ alkoxy, or
e) aryl;

$R^{3a}$ and $R^{3b}$ on adjacent carbons can be joined together to form a benzo group;

$R^4$ and $R^{4a}$ are independently a) $C_{1-3}$ alkyl, b) polyfluoro-$C_{1-3}$ alkyl, c) —CONHR$^1$, d) —CO$_2$R$^1$ or e) —CONH (CH$_2$)$_n$-aryl;

$R^5$ is hydrogen or $C_{1-5}$ alkyl;

In the above definitions, aryl is meant to include phenyl, naphthyl and 2-, 3-, or 4-pyridyl.

The terms "alkyl" and "alkoxy", include both straight- and branched-chain groups where the number of carbons permit.

One embodiment of the novel compounds is that wherein $R^4$ and $R^{4a}$ are both $C_{1-3}$ alkyl, especially methyl, and $R^5$ is $C_{1-5}$ alkyl, especially ethyl.

A class of compounds within this embodiment is that wherein $R^2$ is $C_{1-6}$ alkyl, especially n-propyl.

Specific compounds exemplifying the novel compounds of this invention are described in Table I.

TABLE I

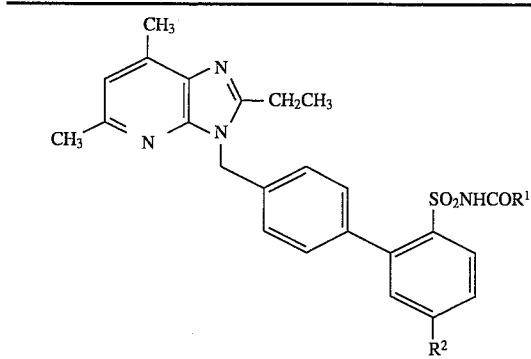

| #(EX) | SO$_2$NHCOR$^1$ | R$^2$ |
|---|---|---|
| 1 | SO$_2$NHCO(CH$_2$)$_4$CH$_3$ | CH$_3$ |
| 2 | SO$_2$NHCO(CH$_2$)$_4$CH$_3$ | CH$_2$CH$_3$ |
| 3 (1) | SO$_2$NHCO(CH$_2$)$_4$CH$_3$ | (CH$_2$)$_2$CH$_3$ |
| 4 | SO$_2$NHCO(CH$_2$)$_4$CH$_3$ | (CH$_2$)$_3$CH$_3$ |
| 5 (8) | SO$_2$NHCO(CH$_2$)$_4$CH$_3$ | CH(CH$_3$)$_2$ |
| 6 (13) | SO$_2$NHCO(CH$_2$)$_4$CH$_3$ | O(CH$_2$)$_3$CH$_3$ |
| 7 | SO$_2$NHCO(CH$_2$)$_4$CH$_3$ | CH$_2$CH(CH$_3$)$_2$ |
| 8 | SO$_2$NHCO(CH$_2$)$_4$CH$_3$ | OCH$_3$ |
| 9 | SO$_2$NHCO(CH$_2$)$_4$CH$_3$ | CH$_2$SCH$_3$ |
| 10 | SO$_2$NHCO(CH$_2$)$_4$CH$_3$ | CH$_2$OCH$_3$ |
| 11 | SO$_2$NHCO(CH$_2$)$_4$CH$_3$ | OCH$_2$CH$_3$ |
| 12 | SO$_2$NHCO(CH$_2$)$_4$CH$_3$ | Ph |
| 13 | SO$_2$NHCO(CH$_2$)$_4$CH$_3$ | C(CH$_3$)$_2$CH$_2$CH$_3$ |
| 14 | SO$_2$NHCO(CH$_2$)$_4$CH$_3$ | C(CH$_3$)$_3$ |
| 15 (6) | SO$_2$NHCO(CH$_2$)$_4$CH$_3$ | CH$_2$N(CH$_3$)$_2$ |
| 16 (11) | SO$_2$NHCO(CH$_2$)$_4$CH$_3$ | CH$_2$N(CH$_2$CH$_2$)$_2$ |
| 17 (12) | SO$_2$NHCO(CH$_2$)$_4$CH$_3$ | CH$_2$N(CH$_2$CH$_2$)$_2$O |
| 18 | SO$_2$NHCO(CH$_2$)$_4$CH$_3$ | OCH$_2$CF$_3$ |
| 19 | SO$_2$NHCO(CH$_2$)$_4$CH$_3$ | OCH(CH$_3$)$_2$ |
| 20 | SO2NHCO(CH2)4CH$_3$ | SCH$_2$CH$_3$ |
| 21 | SO$_2$NHCOCH$_2$O(CH$_2$)$_3$CH$_3$ | CH$_3$ |
| 22 | SO$_2$NHCOCH$_2$O(CH$_2$)$_3$CH$_3$ | CH$_2$CH$_3$ |
| 23 (10) | SO$_2$NHCOCH$_2$O(CH$_2$)$_3$CH$_3$ | (CH$_2$)$_2$CH$_3$ |
| 24 | SO$_2$NHCOCH$_2$O(CH$_2$)$_3$CH$_3$ | (CH$_2$)$_3$CH$_3$ |
| 25 | SO$_2$NHCOCH$_2$O(CH$_2$)$_3$CH$_3$ | CH(CH$_3$)$_2$ |
| 26 | SO$_2$NHCOCH$_2$O(CH$_2$)$_3$CH$_3$ | O(CH$_2$)$_3$CH$_3$ |
| 27 | SO$_2$NHCOCH$_2$O(CH$_2$)$_3$CH$_3$ | CH$_2$CH(CH$_3$)$_2$ |
| 28 | SO$_2$NHCOCH$_2$O(CH$_2$)$_3$CH$_3$ | OCH$_3$ |
| 29 | SO$_2$NHCOCH$_2$O(CH$_2$)$_3$CH$_3$ | CH$_2$SCH$_3$ |
| 30 | SO$_2$NHCOCH$_2$O(CH$_2$)$_3$CH$_3$ | CH$_2$OCH$_3$ |
| 31 | SO$_2$NHCOCH$_2$O(CH$_2$)$_3$CH$_3$ | OCH$_2$CH$_3$ |
| 32 | SO$_2$NHCOCH$_2$O(CH$_2$)$_3$CH$_3$ | Ph |

TABLE I-continued

| #(EX) | SO$_2$NHCOR$^1$ | R$^2$ |
|---|---|---|
| 33 | SO$_2$NHCOCH$_2$O(CH$_2$)$_3$CH$_3$ | C(CH$_3$)$_2$CH$_2$CH$_3$ |
| 34 | SO$_2$NHCOCH$_2$O(CH$_2$)$_3$CH$_3$ | C(CH$_3$)$_3$ |
| 35 | SO$_2$NHCOCH$_2$O(CH$_2$)$_3$CH$_3$ | CH$_2$N(CH$_3$)$_2$ |
| 36 | SO$_2$NHCOCH$_2$O(CH$_2$)$_3$CH$_3$ | CH$_2$N(CH$_2$CH$_2$)$_2$ |
| 37 | SO$_2$NHCOCH$_2$O(CH$_2$)$_3$CH$_3$ | CH$_2$N(CH$_2$CH$_2$)$_2$O |
| 38 | SO$_2$NHCOCH$_2$O(CH$_2$)$_3$CH$_3$ | OCH$_2$CF$_3$ |
| 39 | SO$_2$NHCOCH$_2$O(CH$_2$)$_3$CH$_3$ | OCH(CH$_3$)$_2$ |
| 40 | SO$_2$NHCOCH$_2$O(CH$_2$)$_3$CH$_3$ | SCH$_2$CH$_3$ |
| 41 | SO$_2$NHCOCH$_2$OCH$_2$CH$_3$ | CH$_3$ |
| 42 | SO$_2$NHCOCH$_2$OCH$_2$CH$_3$ | CH$_2$CH$_3$ |
| 43 (9) | SO$_2$NHCOCH$_2$OCH$_2$CH$_3$ | (CH$_2$)$_2$CH$_3$ |
| 44 | SO$_2$NHCOCH$_2$OCH$_2$CH$_3$ | (CH$_2$)$_3$CH$_3$ |
| 45 | SO$_2$NHCOCH$_2$OCH$_2$CH$_3$ | CH(CH$_3$)$_2$ |
| 46 | SO$_2$NHCOCH$_2$OCH$_2$CH$_3$ | O(CH$_2$)$_3$CH$_3$ |
| 47 | SO$_2$NHCOCH$_2$OCH$_2$CH$_3$ | CH$_2$CH(CH$_3$)$_2$ |
| 48 | SO$_2$NHCOCH$_2$OCH$_2$CH$_3$ | OCH$_3$ |
| 49 | SO$_2$NHCOCH$_2$OCH$_2$CH$_3$ | CH$_2$SCH3 |
| 50 | SO$_2$NHCOCH$_2$OCH$_2$CH$_3$ | CH$_2$OCH$_3$ |
| 51 | SO$_2$NHCOCH$_2$OCH$_2$CH$_3$ | OCH$_2$CH$_3$ |
| 52 | SO$_2$NHCOCH$_2$OCH$_2$CH$_3$ | Ph |
| 53 | SO$_2$NHCOCH$_2$OCH$_2$CH$_3$ | C(CH$_3$)$_2$CH$_2$CH$_3$ |
| 54 | SO$_2$NHCOCH$_2$OCH$_2$CH$_3$ | C(CH$_3$)$_3$ |
| 55 | SO$_2$NHCOCH$_2$OCH$_2$CH$_3$ | CH$_2$N(CH$_3$)$_2$ |
| 56 | SO$_2$NHCOCH$_2$OCH$_2$CH$_3$ | CH$_2$N(CH$_2$CH$_2$)$_2$ |
| 57 | SO$_2$NHCOCH$_2$OCH$_2$CH$_3$ | CH$_2$N(CH$_2$CH$_2$)$_2$O |
| 58 | SO$_2$NHCOCH$_2$OCH$_2$CH$_3$ | OCH$_2$CF$_3$ |
| 59 | SO$_2$NHCOCH$_2$OCH$_2$CH$_3$ | OCH(CH$_3$)$_2$ |
| 60 | SO$_2$NHCONH(CH$_2$)$_3$CH$_3$ | SCH$_2$CH$_3$ |
| 61 | SO$_2$NHCONH(CH$_2$)$_3$CH$_3$ | CH$_3$ |
| 62 | SO$_2$NHCONH(CH$_2$)$_3$CH$_3$ | CH$_2$CH$_3$ |
| 63 | SO$_2$NHCONH(CH$_2$)$_3$CH$_3$ | (CH$_2$)$_2$CH$_3$ |
| 64 | SO$_2$NHCONH(CH$_2$)$_3$CH$_3$ | (CH$_2$)$_3$CH$_3$ |
| 65 | SO$_2$NHCONH(CH$_2$)$_3$CH$_3$ | CH(CH$_3$)$_2$ |
| 66 | SO$_2$NHCONH(CH$_2$)$_3$CH$_3$ | O(CH$_2$)$_3$CH$_3$ |
| 67 | SO$_2$NHCONH(CH$_2$)$_3$CH$_3$ | CH$_2$CH(CH$_3$)$_2$ |
| 68 | SO$_2$NHCONH(CH$_2$)$_3$CH$_3$ | OCH$_3$ |
| 69 | SO$_2$NHCONH(CH$_2$)$_3$CH$_3$ | CH$_2$SCH$_3$ |
| 70 | SO$_2$NHCONH(CH$_2$)$_3$CH$_3$ | CH$_2$OCH$_3$ |
| 71 | SO$_2$NHCONH(CH$_2$)$_3$CH$_3$ | OCH$_2$CH$_3$ |
| 72 | SO$_2$NHCONH(CH$_2$)$_3$CH$_3$ | Ph |
| 73 | SO$_2$NHCONH(CH$_2$)$_3$CH$_3$ | C(CH$_3$)$_2$CH$_2$CH$_3$ |
| 74 | SO$_2$NHCONH(CH$_2$)$_3$CH$_3$ | C(CH$_3$)$_3$ |
| 75 | SO$_2$NHCONH(CH$_2$)$_3$CH$_3$ | CH$_2$N(CH$_3$)$_2$ |
| 76 | SO$_2$NHCONH(CH$_2$)$_3$CH$_3$ | CH$_2$N(CH$_2$CH$_2$)$_2$ |
| 77 | SO$_2$NHCONH(CH$_2$)$_3$CH$_3$ | CH$_2$N(CH$_2$CH$_2$)$_2$O |
| 78 | SO$_2$NHCONH(CH$_2$)$_3$CH$_3$ | OCH$_2$CF$_3$ |
| 79 | SO$_2$NHCONH(CH$_2$)$_3$CH$_3$ | OCH(CH$_3$)$_2$ |
| 80 | SO$_2$NHCONH(CH$_2$)$_3$CH$_3$ | SCH$_2$CH$_3$ |
| 81 | SO$_2$NHCO(CH$_2$)$_2$Ph | CH$_3$ |
| 82 | SO$_2$NHCO(CH$_2$)$_2$Ph | CH$_2$CH$_3$ |
| 83 (3) | SO$_2$NHCO(CH$_2$)$_2$Ph | (CH$_2$)$_2$CH$_3$ |
| 84 | SO$_2$NHCO(CH$_2$)$_2$Ph | (CH$_2$)$_3$CH$_3$ |
| 85 | SO$_2$NHCO(CH$_2$)$_2$Ph | CH(CH$_3$)$_2$ |
| 86 | SO$_2$NHCO(CH$_2$)$_2$Ph | O(CH$_2$)$_3$CH$_3$ |
| 87 | SO$_2$NHCO(CH$_2$)$_2$Ph | CH$_2$CH(CH$_3$)$_2$ |
| 88 | SO$_2$NHCO(CH$_2$)$_2$Ph | OCH$_3$ |
| 89 | SO$_2$NHCO(CH$_2$)$_2$Ph | CH$_2$SCH$_3$ |
| 90 | SO$_2$NHCO(CH$_2$)$_2$Ph | CH$_2$OCH$_3$ |
| 91 | SO$_2$NHCO(CH$_2$)$_2$Ph | OCH$_2$CH$_3$ |

TABLE I-continued

| #(EX) | SO$_2$NHCOR$^1$ | R$^2$ |
|---|---|---|
| 92 | SO$_2$NHCO(CH$_2$)$_2$Ph | Ph |
| 93 | SO$_2$NHCO(CH$_2$)$_2$Ph | C(CH$_3$)$_2$CH$_2$CH$_3$ |
| 94 | SO$_2$NHCO(CH$_2$)$_2$Ph | C(CH$_3$)$_3$ |
| 95 | SO$_2$NHCO(CH$_2$)$_2$Ph | CH$_2$N(CH$_3$)$_2$ |
| 96 | SO$_2$NHCO(CH$_2$)$_2$Ph | CH$_2$N(CH$_2$CH$_2$)$_2$ |
| 97 | SO$_2$NHCO(CH$_2$)$_2$Ph | CH$_2$N(CH$_2$CH$_2$)$_2$O |
| 98 | SO$_2$NHCO(CH$_2$)$_2$Ph | OCH$_2$CF$_3$ |
| 99 | SO$_2$NHCO(CH$_2$)$_2$Ph | OCH(CH$_3$)$_2$ |
| 100 | SO$_2$NHCO(CH$_2$)$_2$Ph | SCH$_2$CH$_3$ |
| 101 | SO$_2$NHCO(2-PhO)Ph | CH$_3$ |
| 102 | SO$_2$NHCO(2-PhO)Ph | CH$_2$CH$_3$ |
| 103 (4) | SO$_2$NHCO(2-PhO)Ph | (CH$_2$)$_2$CH$_3$ |
| 104 | SO$_2$NHCO(2-PhO)Ph | CH(CH$_3$)$_2$ |
| 105 | SO$_2$NHCO(2-PhO)Ph | O(CH$_2$)$_3$CH$_3$ |
| 106 | SO$_2$NHCO(2-PhO)Ph | CH$_2$CH(CH$_3$)$_2$ |
| 107 | SO$_2$NHCO(2-PhO)Ph | OCH$_3$ |
| 108 | SO$_2$NHCO(2-PhO)Ph | CH$_2$SCH$_3$ |
| 109 | SO$_2$NHCO(2-PhO)Ph | CH$_2$OCH$_3$ |
| 110 | SO$_2$NHCO(2-PhO)Ph | OCH$_2$CH$_3$ |
| 111 | SO$_2$NHCO(2-PhO)Ph | Ph |
| 112 | SO$_2$NHCO(2-PhO)Ph | C(CH$_3$)$_2$CH$_2$CH$_3$ |
| 113 | SO$_2$NHCO(2-PhO)Ph | C(CH$_3$)$_3$ |
| 114 | SO$_2$NHCO(2-PhO)Ph | CH$_2$N(CH$_3$)$_2$ |
| 115 | SO$_2$NHCO(2-PhO)Ph | CH$_2$N(CH$_2$CH$_2$)$_2$ |
| 116 | SO$_2$NHCO(2-PhO)Ph | CH$_2$N(CH$_2$CH$_2$)$_2$O |
| 117 | SO$_2$NHCO(2-PhO)Ph | OCH$_2$CF$_3$ |
| 118 | SO$_2$NHCO(2-PhO)Ph | OCH(CH$_3$)$_2$ |
| 119 | SO$_2$NHCO(2-PhO)Ph | SCH$_2$CH$_3$ |
| 120 | SO$_2$NHCO(2-EtO)Ph | CH$_3$ |
| 121 | SO$_2$NHCO(2-EtO)Ph | CH$_2$CH$_3$ |
| 122 | SO$_2$NHCO(2-EtO)Ph | (CH$_2$)$_2$CH$_3$ |
| 123 | SO$_2$NHCO(2-EtO)Ph | CH(CH$_3$)$_2$ |
| 124 | SO$_2$NHCO(2-EtO)Ph | O(CH$_2$)$_3$CH$_3$ |
| 125 | SO$_2$NHCO(2-EtO)Ph | CH$_2$CH(CH$_3$)$_2$ |
| 126 | SO$_2$NHCO(2-EtO)Ph | OCH$_3$ |
| 127 | SO$_2$NHCO(2-EtO)Ph | CH$_2$SCH$_3$ |
| 128 | SO$_2$NHCO(2-EtO)Ph | CH$_2$OCH$_3$ |
| 129 | SO$_2$NHCO(2-EtO)Ph | OCH$_2$CH$_3$ |
| 130 | SO$_2$NHCO(2-EtO)Ph | Ph |
| 131 | SO$_2$NHCO(2-EtO)Ph | C(CH$_3$)$_2$CH$_2$CH$_3$ |
| 132 | SO$_2$NHCO(2-EtO)Ph | C(CH$_3$)$_3$ |
| 133 | SO$_2$NHCO(2-EtO)Ph | CH$_2$N(CH$_3$)$_2$ |
| 134 | SO$_2$NHCO(2-EtO)Ph | CH$_2$N(CH$_2$CH$_2$)$_2$ |
| 135 | SO$_2$NHCO(2-EtO)Ph | CH$_2$N(CH$_2$CH$_2$)$_2$O |
| 136 | SO$_2$NHCO(2-EtO)Ph | OCH$_2$CF$_3$ |
| 137 | SO$_2$NHCO(2-EtO)Ph | OCH(CH$_3$)$_2$ |
| 138 | SO$_2$NHCO(2-EtO)Ph | SCH$_2$CH$_3$ |
| 139 | SO$_2$NHCOPh | CH$_3$ |
| 140 | SO$_2$NHCOPh | CH$_2$CH$_3$ |
| 141 (5) | SO$_2$NHCOPh | (CH$_2$)$_2$CH$_3$ |
| 142 | SO$_2$NHCOPh | CH(CH$_3$)$_2$ |
| 143 | SO$_2$NHCOPh | O(CH$_2$)$_3$CH$_3$ |
| 144 | SO$_2$NHCOPh | CH$_2$N(CH$_3$)$_2$ |
| 145 | SO$_2$NHCOPh | OCH$_3$ |
| 146 | SO$_2$NHCOPh | CH$_2$SCH$_3$ |
| 147 | SO$_2$NHCOPh | CH$_2$OCH$_3$ |
| 148 | SO$_2$NHCOPh | OCH$_2$CH$_3$ |
| 149 | SO$_2$NHCOPh | Ph |
| 150 | SO2NHCOPh | C(CH$_3$)$_2$CH$_2$CH$_3$ |
| 151 | SO2NHCOPh | C(CH$_3$)$_3$ |
| 152 | SO2NHCOPh | CH$_2$N(CH$_3$)$_2$ |
| 153 | SO2NHCOPh | CH$_2$N(CH$_2$CH$_2$)$_2$ |
| 154 | SO$_2$NHCOPh | CH$_2$N(CH$_2$CH$_2$)$_2$O |
| 155 | SO$_2$NHCOPh | OCH$_2$CF$_3$ |
| 156 | SO$_2$NHCOPh | OCH(CH$_3$)$_2$ |
| 157 | SO$_2$NHCOPh | SCH$_2$CH$_3$ |
| 158 | SO$_2$NHCOCH$_2$O(CH$_2$)$_2$CH$_3$ | CH$_3$ |
| 159 | SO$_2$NHCOCH$_2$O(CH$_2$)$_2$CH$_3$ | CH$_2$CH$_3$ |
| 160 | SO$_2$NHCOCH$_2$O(CH$_2$)$_2$CH$_3$ | (CH$_2$)$_2$CH$_3$ |
| 161 | SO$_2$NHCOCH$_2$O(CH$_2$)$_2$CH$_3$ | CH(CH$_3$)$_2$ |
| 162 | SO$_2$NHCOCH$_2$O(CH$_2$)$_2$CH$_3$ | O(CH$_2$)$_3$CH$_3$ |
| 163 | SO$_2$NHCOCH$_2$O(CH$_2$)$_2$CH$_3$ | OCH$_3$ |
| 164 | SO$_2$NHCOCH$_2$O(CH$_2$)$_2$CH$_3$ | CH$_2$SCH$_3$ |
| 165 | SO$_2$NHCOCH$_2$O(CH$_2$)$_2$CH$_3$ | CH$_2$OCH$_3$ |
| 166 | SO$_2$NHCOCH$_2$O(CH$_2$)$_2$CH$_3$ | OCH$_2$CH$_3$ |
| 167 | SO$_2$NHCOCH$_2$O(CH$_2$)$_2$CH$_3$ | Ph |
| 168 | SO$_2$NHCOCH$_2$O(CH$_2$)$_2$CH$_3$ | C(CH$_3$)$_2$CH$_2$CH$_3$ |
| 169 | SO$_2$NHCOCH$_2$O(CH$_2$)$_2$CH$_3$ | C(CH$_3$)$_3$ |
| 170 | SO$_2$NHCOCH$_2$O(CH$_2$)$_2$CH$_3$ | CH$_2$N(CH$_3$)$_2$ |
| 171 | SO$_2$NHCOCH$_2$O(CH$_2$)$_2$CH$_3$ | CH$_2$N(CH$_2$CH$_2$)$_2$ |
| 172 | SO$_2$NHCOCH$_2$O(CH$_2$)$_2$CH$_3$ | CH$_2$N(CH$_2$CH$_2$)$_2$O |
| 173 | SO$_2$NHCOCH$_2$O(CH$_2$)$_2$CH$_3$ | OCH$_2$CF$_3$ |

Scheme Descriptions

The general procedure used to prepare many of the 5'-substituted derivatives is illustrated in Scheme I. Commercially available 4-substituted benzenesulfonyl chlorides (R$^2$=i-Pr, n-BuO, tert-amyl, Me, Et, n-Pr, t-Bu) are reacted with t-BuNH$_2$ in CH$_2$Cl$_2$ or CHCl$_3$ to provide derivative 2 in good yield. Dianion generation in THF, with 2.5 equivalents of n-BuLi, followed by quench with triisopropyl borate provides boric acid derivative 3 in excellent yield, after hydrolysis with dilute acid. Palladium catalyzed coupling of boric acid 3 and 4-bromobenzyl derivative 4 in the presence of 1.25N NaOH, EtOH and toluene, affords an excellent yield of the desired coupled product. Deprotection using TFA is followed by coupling using methods A or B with the appropriate acid or acid chloride to prepare acylsulfonamides and method C with the appropriate isocyanate to prepare sulfonylureas.

When the desired 4-substituted benzenesulfonyl chlorides are not commercially available, the necessary 4-substituted benzenetbutylsulfonamide (2) derivatives can be prepared using a variety of procedures. These procedures are outlined in Scheme II (A–F). In Scheme II A, a variety of trimethylstannyl derivatives could be coupled to aryl bromide 8 in the presence of Pd(PPh$_3$)$_4$ or PdCl$_2$(PPh$_3$)$_2$. In this example this is followed by hydrogenation to obtain the isobutyl derivative. Introduction of an aryl ring is best accomplished using the palladium catalyzed boric acid coupling method illustrated in Scheme II B. Thiomethyl and aminomethyl derivatives are both prepared from bromomethyl derivative 11 as illustrated in Schemes II C and D receptively. A convenient manner to introduce alkoxy substituents is illustrated in Scheme II E. An alternative procedure to prepare alkyl derivatives starting with an alkylbenzene is illustrated in Scheme II F.

Antagonists with 5'-alkoxy methyl derivatives are best prepared using the protocol outlined in Scheme III. Palladium catalyzed coupling of 5-methyl-2-t-butylsulfonamide phenylboric acid with methyl 4-iodobenzoate affords derivative 12. Benzylic bromination, utilizing NBS in refluxng $CCl_4$, with a catalytic amount of AIBN or alternatively, benzoyl peroxide, provides the desired bromomethyl derivative that is then reacted with the appropriate sodium alkoxide to afford derivative 14. Reduction of the ester to the primary alcohol with LAH is followed by conversion to the bromomethyl derivative (16) with $PBr_3$. Alkylation of the sodium salt of the heterocycle with 16 in DMF provides derivative 6 ($R^2=CH_2OR$). The antagonist is completed as previously illustrated in Scheme I.

Introduction of substituents into the central phenyl of the biphenyl moiety is best accomplished using the protocol illustrated in scheme IV. Palladium catalyzed coupling of 5-substituted-2-t-butylsulfonamide phenylboric acid with a substituted methyl 4-iodobenzoate or bromobenzoate affords derivative 17. Reduction of the ester to the primary alcohol with LAH is followed by conversion to the bromomethyl derivative (19) with $PBr_3$. Alkylation of the sodium salt of the heterocycle with 19 in DMF provides derivative 6. The antagonist is completed as previously illustrated in Scheme I.

SCHEME I

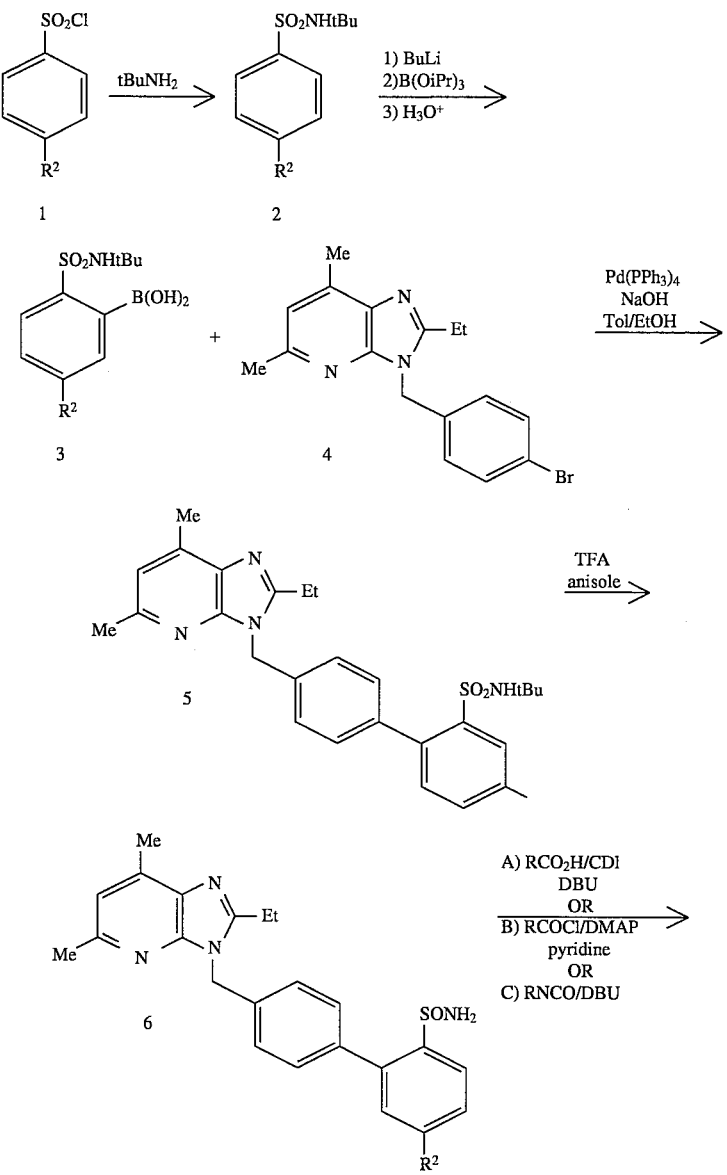

-continued
SCHEME I
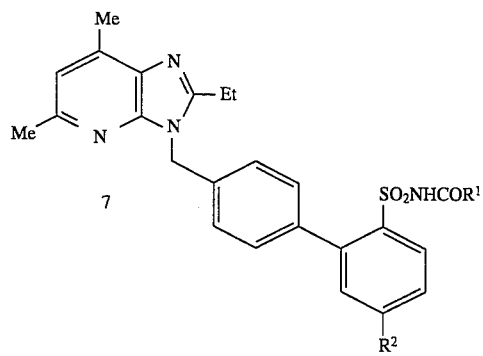
SCHEME II
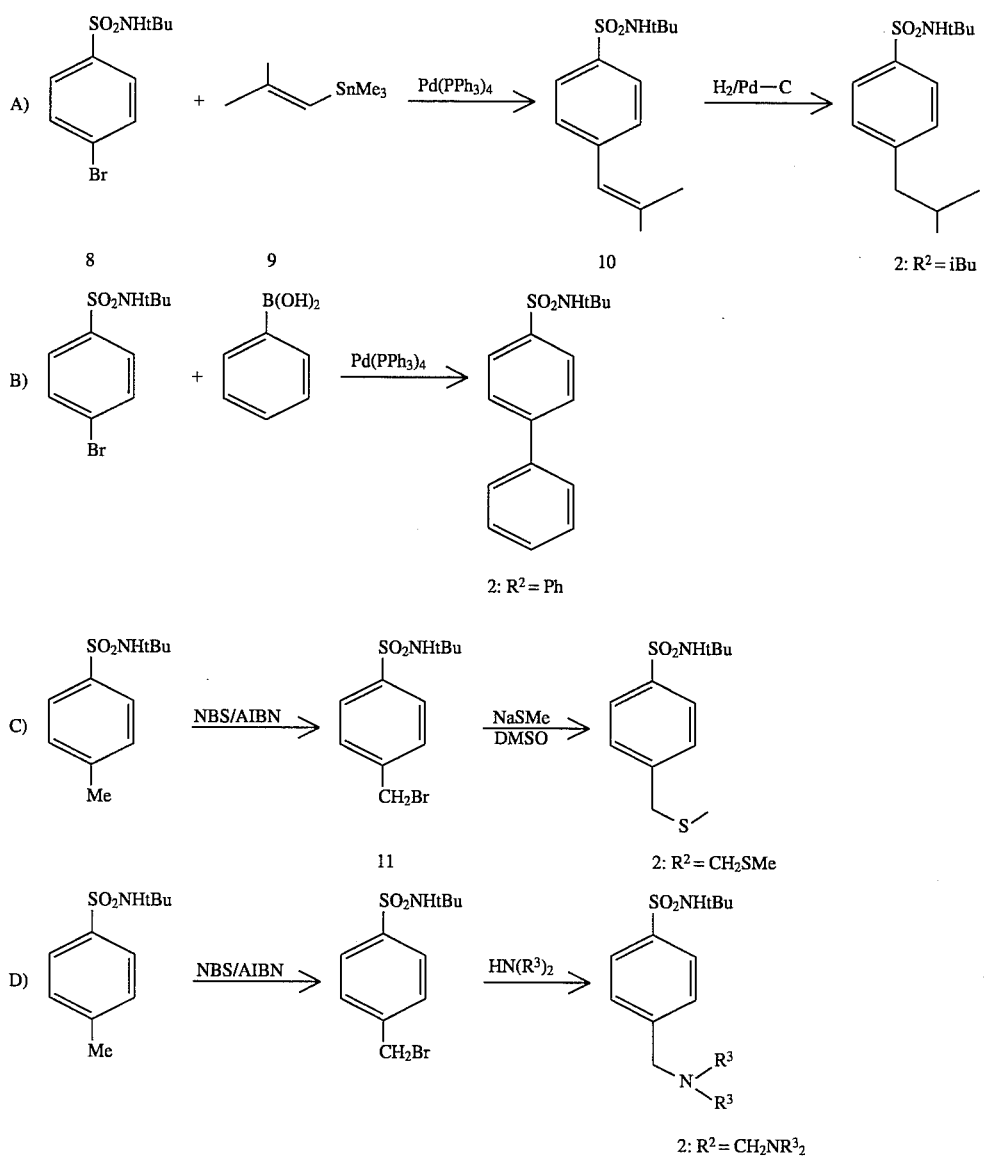

-continued
SCHEME II
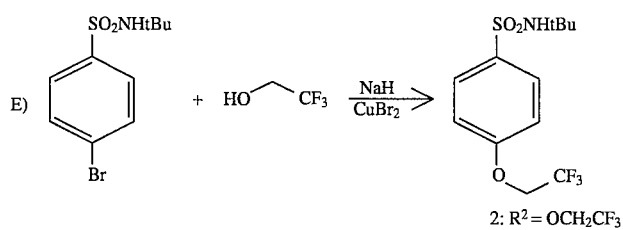
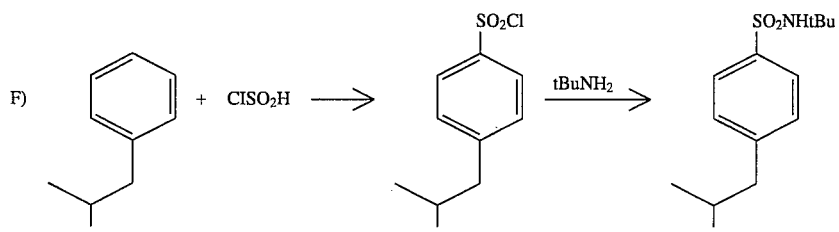
SCHEME III
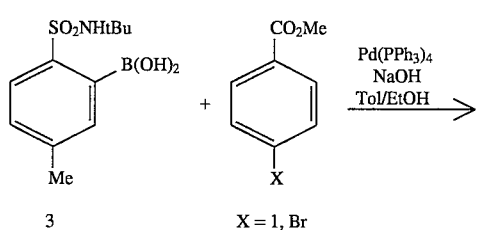
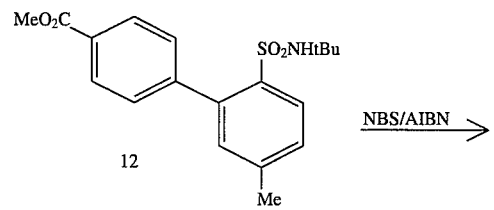
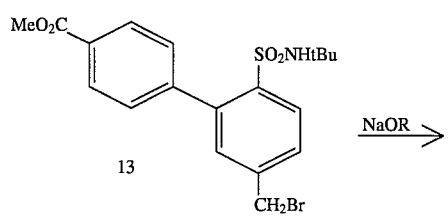
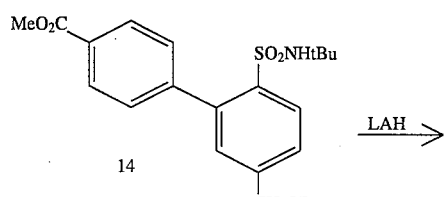
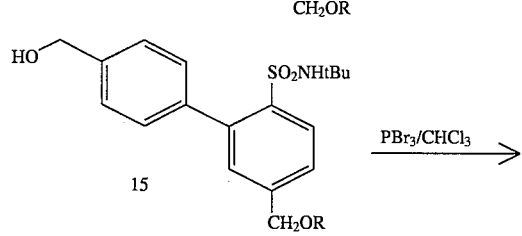
-continued
SCHEME III
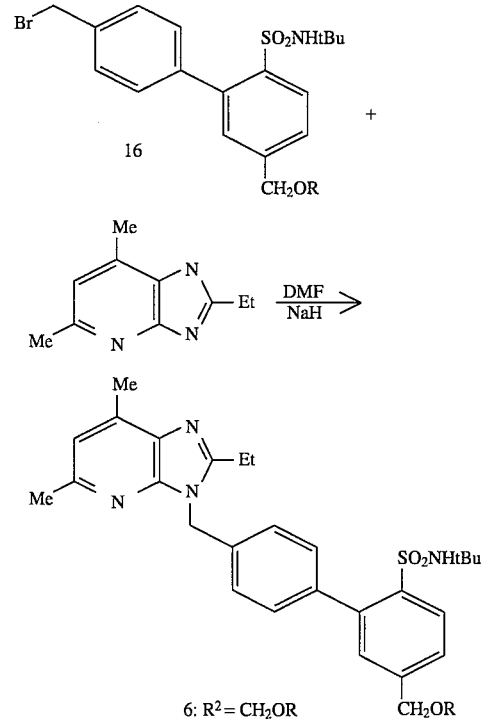
SCHEME IV
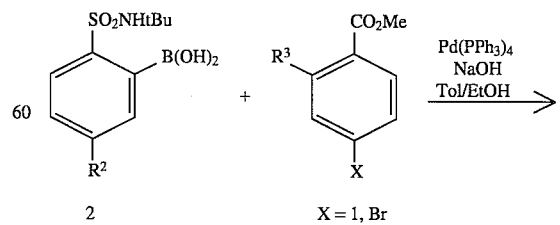

13

-continued
SCHEME IV

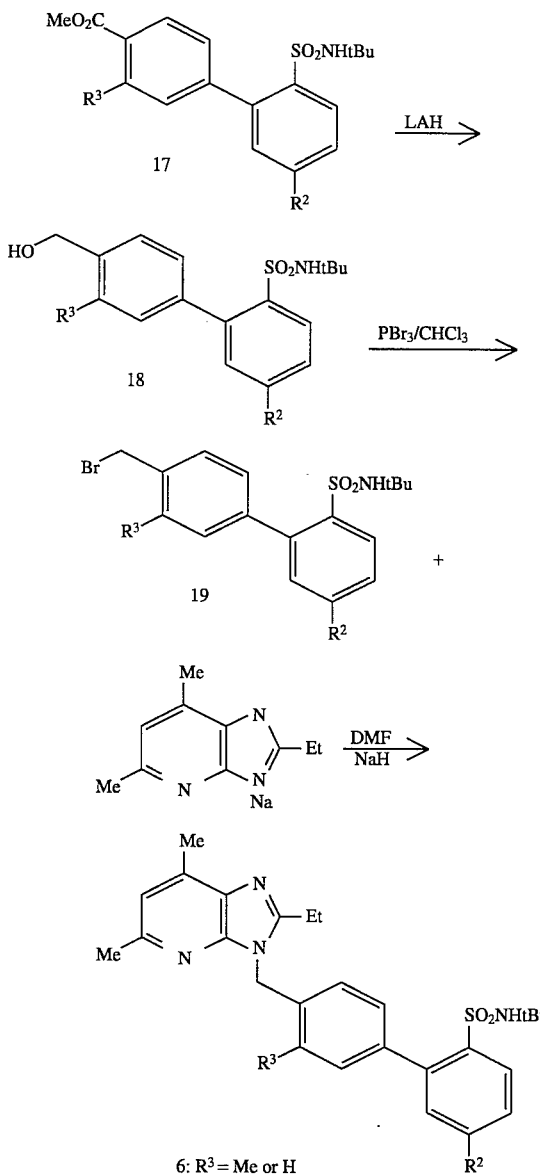

6: R³ = Me or H

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

14

Angiotensin II (A II) is a powerful arterial vasoconstrictor, and it exerts its action by interacting with specific receptors present on cell membranes. The compounds described in the present invention act as competitive antagonists of A II at the receptors. In order to identify A II antagonists and determine their efficacy in vitro, the following three ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 µl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential A II antagonist which gives 50% displacement of the total specifically bound $^{125}$I-Sar$^1$Ile$^8$-angiotensin II was presented as a measure of the efficacy of such compounds as A II antagonists.

Receptor Assay Using Bovine Adrenal Cortex Preparation

Bovine adrenal cortex was selected as the source of A II receptor. Weighed tissue (0.1 g is needed for 100 assay tubes) was suspended in Tris.HCl (50 mM), pH 7.7 buffer end homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added $^3$H-angiotensin II (50 mM) (10 µl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential A II antagonist which gives 50% displacement of the total specifically bound $^3$H-angiotensin II was presented as a measure of the efficacy of such compounds as A II antagonists.

Receptor Assay Using Rat Brain Membrane Preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NaCl, 10 mM Na$_2$HPO$_4$, 5 mM Na$_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding; assays, 10 µl of solvent (for total binding), Sar$^1$,Ile$^8$-angiotensin II (1 µM) (for nonspecific binding) or test compounds (for displacement) and 10 µl of [$^{125}$I]Sar$^1$,Ile$^8$-angiotensin II (23–46 pM) were added to duplicate tubes. The receptor membrane preparation (500 µl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate— 60 strokes per minute, volume— 1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and all were found to exhibit an activity of at least IC$_{50}$ 10 µM against the AT$_1$ and AT$_2$ subtype receptors thereby demonstrating and confirming the utility of the compounds of the invention as effective A II antagonists with "balanced" AT$_1$/AT$_2$ activity.

Thus, the compounds of the invention are useful in treating hypertension. They are also of value in the management of acute and chronic congestive heart failure and angina. These compounds are also expected to be useful in primary and secondary hyperaldosteronism, renal diseases such as diabetic nephropathy, glomerulonephritis, glomerular sclerosis, nephrotic syndrome, hypertensive nephrosclerosis, end stage renal disease, renal transplant therapy, renovascular hypertension, scleroderma, left ventricular dysfunction, systolic and diastolic dysfunction diabetic retinopathy, in the management of vascular disorders such as migraine or Raynaud's disease, as prophylaxis to minimize the atherosclerotic process, in neointimal hyperplasia follwoing angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, β-adrenergic antagonists such as timolol maleate, adrenergic agonists such as epinephrine and carbonic anhydrase inhibitors such as TRUSOPT™.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about: 1 to 1000 mg. per patient per day which can be administered in single or multiple doses. Perferably, the dosage range will be about 5.0 to 500 mg. per patient per day; more preferably about 5 to 300 mg. per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methyclothiazide, furosemide, ethacrynic acid, triamterene, amiloride; atriopeptin and spironolactone; calcium channel blockers, such as diltiazem, felodipine, nifedipine, amlodipine, nimodipine, isradipinei nitrendipine and verapamil; β-adrenergic antagonists such as timolol, atenolol, metoprolol, propanolol; nadolol and pindolol; angiotensin converting enzyme inhibitors such as enalapril, lisinopril, captopril, ramipril, quinapril and zofenopril; renin inhibitors such as A-69729 and FK 906 and FK 744; α-adrenergic antagonists such as prazosin, doxazosin, and terazosin; sympatholytic agents such as methyldopa, clonidine and guanabenz, atriopeptidase inhibitors (alone or with ANP) such as UK-79300; serotonin antagonists such as ketanserin; A$_2$-adenosine receptoragonists such as CGS 22492C; potassium channel agonists such as pinacidil and cromakalim; and various other antihypertensive drugs including resetpine, minoxidil, guanethidine, hydralazine hydrochloride and sodium nitroprusside as well as combinations of the above-named drugs.

Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 5–500 milligrams per day range can be effectively combined at levels of the 1.0–500 milligrams per day range with the following compounds at the indicated per day dose range: hydrochlorothiazide (6–100 mg), chlorothiazide (125–500 mg), ethacrynic acid (5–200 mg), amiloride (5–20 mg), furosemide (5–80 mg), propanolol (10–480 mg), timolol maleate (1–20 mg), methyldopa (125–2000 mg), felodipine (1–20 mg), nifedipine (5–120 mg), nitrendipine (5–60 mg) and diltiazem (30–540 mg). In addition, triple drug combinations of hydrochlorothiazide (5–100 mg) plus amiloride (5–20 mg) plus an angiotensin II antagonist of this invention (1–500 mg) or hydrochlorothiazide (5–100 mg) plus timolol maleate (5–60) plus an angiotensin II antagonist of this invention (1–500 mg) or hydrochlorothiazide (5–200 mg) and nifedipine (5–60 mg) plus an angiotensin II antagonist of this invention (1–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

EXAMPLE 1

5,7-dimethyl-2-ethyl-3[[2'-(N-n-pentylcarbonylsulfonamido)-5'-n-propyl[1,1'biphenyl]-4-yl]methylimidazo[4,5-b]pyridine (Compound 3 of Table 1)

Step A: Preparation of 4-n-propylbenzene-t-butylsulfonamide (Scheme I, compound 2, $R^2$=n-pr)

To a solution of 4-n-propylphenylsulfonyl chloride (Lancaster) in anhydrous $CH_2Cl_2$ (0.5M solution) cooled to 0° C. under $N_2$ was added t-butylamine (2.2 equiv) slowly through a dropping funnel. After complete addition, the reaction was stirred at rt for 12 h. The $CH_2Cl_2$ was removed under reduced pressure and the residue was extracted into $Et_2O$ and washed with 2N NaOH, $H_2O$ and brine. The organic was dried over anhydrous $MgSO_4$ and concentrated in vacuo to afford the titled product. Rf=0.46 (3:1 Hex/EtOAc).

$^1$H NMR (200 MHz, $CDCl_3$) δ 0.93 (t, 3H), 1.22 (s, 9H), 1.62 (m, 2H), 2.65 (t, 2H), 4.67 (bs, 1H), 7.27 (d, 2H), 7.79 (d, 2H).

Step B: Preparation of 2-t-butylsulfonamido-5-n-propylphenylboric Acid (Scheme I, compound 3. $R^2$=n-pr)

To a solution of 4-n-propylphenyl-t-butylsulfonamide (2.85 g, 11.2 mmoL) in anhydrous THF (20 mL) cooled to –40° C. under $N_2$ was added 2.5M n-BuLi solution (11.2 mL, 2.5 equiv). The mixture was warmed to rt and stirred for 2 h. To the mixture, containing the bright red dianion at 0° C., was added $B(OiPr)_3$ (3.9 mL, 1.5 equiv). The next day 2N HCl (3 mL) was added and the mixtue was stirred for 1 h. The solvent was removed under reduced pressure and the residue was extracted With EtOAc. The organic was washed with 2N HCl, $H_2O$ and brine. The organic was dried over anhydrous $MgSO_4$ and concentrated in vacuo to afford the titled compound. Rf=0.5 (1:1 EtOAc/Hex). The crude material was used in subsequent steps without further purification.

Step C: Preparation of 5,7-dimethyl-2-ethyl-3[[2'-(N-tbutylsulfonamido)-5'-n-propyl-[1,1'biphenyl]-4-yl]methylimidazo[4,5-b]pyridine (Scheme I, compound 5, $R^2$=n-pr)

To a solution of 5,7-dimethyl-2-ethyl-3[[4bromo]phenyl]methylimidazo[4,5-b]pyridine (6.0 g, 17.4 mmol) and the product of step B (11.2 g, 37.3 mmol) in toluene (230 mL) was added 1.25N NaOH (58 mL), EtOH (160 mL) and $Pd(PPh_3)_4$ (1.25 g, 3 mol %). The reaction mixture was stirred at 100° C. under $N_2$ for 2 h. The solvent was removed under reduced pressure and the residue was taken up in EtOAc. The organic was washed with 1N NaOH, $H_2O$ and brine and dried over anhydrous $MgSO_4$ and concentrated in vacuo. The titled product was recrystallized from EtOAc/Hex. Rf=0.5 (2:1 EtOAc/Hex).

$^1$H NMR (400 MHz, $CD_3OD$) δ 0.93 (t, 3H), 0.95 (s, 9H), 1.32 (t, 3H), 1.67 (m,52H), 2.58 (s, 3H), 2.61 (s, 3H), 2.66 (t, 2H), 2.91 (q, 2H), 5.61 (s, 2H), 7.03 (s, 1H), 7.09 (d, 1H), 7.18 (d, 2H), 7.32 (dd, 1H), 7.41 (d, 2H), 7.97 (d, 1H).

Step D: Preparation of 5,7-dimethyl-2-ethyl-3[[2'-(sulfonamido)-5'-n-propyl[1,1 'bi-phenyl]-4-yl]methylimidazo[4,5-b]pyridine (Scheme I, compound 5, $R^2$=n-pr)

To a mixture of the product of step C (945 mg, 1.82 mmol) and anisole (0.5 mL) was added TFA (5 mL). After standing at rt for 24 h, the mixture was concentrated in vacuo. The residue was taken up in EtOAc and washed with 2N $Na_2CO_3$ solution, $H_2O$ and brine. The organic was dried over anhydrous $MgSO_4$ and concentrated in vacuo. The titled product, crystallized from Hex/$Et_2O$, was obtained as a white powder. Rf=0.29 (2:1 EtOAc/Hex).

Step E: Preparation of 5,7-dimethyl-2-ethyl-3[[2'-(N-n-pentylcarbonylsulfonamido)-5'-n-propyl [1,1'biphenyl]-4-yl]methylimidazo[4,5-b]pyridine (compound 3 of Table 1)

To a solution of hexanoic acid (23 mg, 0.195 mmol) in dry THF (0.5 mL) under $N_2$ was added CDI (35 mg, 0.22 mmol). The mixture was stirred at 40° C. for 2.5 h. To that solution was added a solution of the product of step D (30 mg, 0.065 mmol) and DBU (0.029 mL, 0.195 mmol) in THF (0.5 mL). The reaction was stirred at 40° C. for ca. 4 h. The reaction was quenched with MeOH (0.25 mL) and stirred for an additional 30 min. The solvent was removed and the the residue was dissolved in EtOAc and washed with 10% citric acid solution, H₂O and brine. The titled product was purified by flash chromatography eluting with 80:10:1 ($CH_2Cl_2$/MeOH/$NH_4OH$) Rf=0.37 (20:1 $CHCl_3$/MeOH).

¹H NMR (400 MHz, $CD_3OD$) δ 0.80 (t, 3H), 0.94 (t, 3H), 1.03 (m, 2H), 1.15 (m, 2H), 1.31 (m, 2H), 1.35 (t, 3H), 1.65 (m, 2H), 1.71 (t, 2H), 2.58 (s, 3H), 2.61 (s, 3H), 2.93 (m, 2H), 5.62 (s, 2H), 7.02 (s, 1H), 7.08 (d, 1H), 7.14 (d, 2H), 7.28 (d, 2H), 7.38 (dd, 1H), 8.05 (d, 1H).

EXAMPLE 2

5,7-dimethyl-2-ethyl-3[[2'-(N-n-butylaminocarbonylsulfonamido)-5'-n-propyl-[1,1'biphenyl]-4-yl]methylimidazo[4,5-b]pyridine (Compound 63 of Table 1)

To a solution of the product of Example 1, step D (75 mg, 0.162 mmol) in dry THF (2 mL) was added DBU (0.048 mL, 2 equiv) and n-butylisocyanate (0.182 mL, 10 equiv). After stirring at rt for 24 h, the solvent was removed under reduced pressure and the residue was dissolved in EtOAc and washed in 10% citric acid solution, H₂O and brine. The organic was dried over anhydrous $MgSO_4$ and concentrated in vacuo. The titled compound was purified by flash chromatography eluting with 80:10:1 ($CH_2Cl_2$/MeOH/$NH_4OH$). Rf=0.68 (40:10:1 $CHCl_3$/MeOH/$NH_4OH$).

¹H NMR (400 MHz, $CD_3OD$) δ 0.80 (t, 3H), 0.94 (t, 3H), 1.13 (m, 2H), 1.23 (m, 2H), 1.31 (t, 3H), 1.67 (m, 2H), 2.58 (s, 3H), 2.62 (s, 3H), 2.65 (t, 2H), 2.91 (m, 4H), 5.61 (s, 2H), 7.02 (s, 1H), 7.08 (s, 1H), 7.12 (d, 2H), 7.28 (d, 2H), 7.37 (d, 1H), 8.01 (d, 1H).

EXAMPLE 3

5,7-dimethyl-2-ethyl-3[[2'-(N-(2-phenylethyl)carbonylsulfonamido)-5'-n-propyl[1,1'biphenyl]-4-yl]methylimidazo[4,5-b]pyridine (Compound 83 of Table 1)

To a solution of hydrocinnamic acid (50 mg, 0.33 mmol) in dry THF :(1 mL) was added CDI (59 mg, 0.36 mmol). The mixture was stirred at 50° C. for 2 h. To that mixture was added a solution of the product of Example 1, step D (50 mg, 0.108 mmol) and DBU (0.050 mL, 0.33 mmoL)in dry THF (1 mL). The reaction was stirred at 50° C. for 12 h then quenched with MeOH (0.25 mL) and concentrated in vacuo. The residue was dissolved in EtOAc and washed with 10% citric acid solution, H₂O and brine. The organic was dried over anhydrous $MgSO_4$ and concentrated in vacuo. The titled product was purified by radial chromatography eluting with 100:10:1 ($CH_2Cl_2$/MeOH/$NH_4OH$). Rf=0.56 (80:10:1 $CHCl_3$/MeOH/$NH_4OH$).

¹H NMR (400 MHz, $CD_3OD$) δ 0.94 (t, 3H), 1.28 (t, 3H), 1.62 (m, 2H), 2.13 (t, 2H), 2.55 (s, 3H), 2.62 (s, 3H), 2.85 (q, 2H), 5.55 (s, 2H), 6.95–7.03 (comp m, 6H), 7.08 (m, 3H), 7.13 (d, 2H), 7.31 (dd, 1H), 8.02 (d, 1H).

EXAMPLE 4

5,7-dimethyl-2-ethyl-3[[2'-(N-(2-phenoxyphenyl)carbonylsulfonamido[4,5-b]pyridine (Compound 103of Table 1)

To a solution of 2-phenoxybenzoic acid acid (138 mg, 0.644 mmol) in dry THF (2 mL) was added CDI (125 mg, 0.71 mmol). The mixture was stirred at 40° C. for 2.5 h. To that mixture was added a solution of the product of Example 1, step I) (100 mg, 0.216 mmol) and DBU (0.10 mL, 0.66 mmoL) in dry THF (2 mL). The reaction was stirred at 40° C. for 3.5 h then quenched with MeOH (0.25 mL) and concentrated in vacuo. The residue was dissolved in EtOAc and washed with 10% citric acid solution, H₂O and brine. The organic was dried over anhydrous $MgSO_4$ and concentrated in vacuo. The titled product was purified by radial chromatography eluting with 100::7:1 ($CH_2Cl_2$/MeOH/$NH_4OH$). Rf=0.42 (2:1 EtOAc/Hex).

¹H NMR (400 MHz, $CD_3OD$) δ 0.91 (t, 3H), 1.26 (t, 3H), 1.62 (m, 2H), 2.55 (s, 3H), 2.61 (s, 3H), 2.71 (q, 2H), 5.50 (s, 2H), 6.72 (d, 1H),. 6.95–7.03 (comp m, 6H), 7.21 (comp m. 6H), 7.43 (d, 1H), 8.12 (d, 1H).

EXAMPLE 5

5,7-dimethyl-2-ethyl-3[[2'-(N-benzenecarbonylsulfonamido)-5'-n-propyl[1,1'biphenyl]-4-yl]methylimidazo [4.5-b]pyridine (Compound 143 of Table 1)

To a solution of the product from Example 1, step D (100 mg, 0.216mmol) in dry pyridine (2 mL) was added DMAP (20 mg) and benzoyl chloride (300 mg, 10 equiv). After stirring for 6 h the reaction was quenched with MeOH (0.5 mL) and the solvent was removed in vacuo. The residue was taken up in EtOAc and washed with 10% citric acid, H₂O and brine. The titled product was purified by flash chromatography eluting with 60:10:1 ($CH_2Cl_2$/MeOH/$NH_4OH$). Rf=0.56 (80:10:1$CHCl_3$/MeOH/$NH_4OH$).

¹H NMR (200 MHz, $CDCl_3$) δ 0.83 (t, 3H), 1.29 (t, 3H), 1.58 (m, 2H), 2.53 (s, 3H), 2.61 (s, 3H), 2.84 (q, 2H), 5.48 (s, 2H), 6.85–7.01 (comp m, 4H), 7.09–7.29 (comp m, 6H), 7.38 (d, 2H), 8.17 (d, 1H).

Examples 6 through 13, shown in Table 2, were prepared using procedures described in the previous five examples and illustrated in Schemes I through IV.

TABLE 2

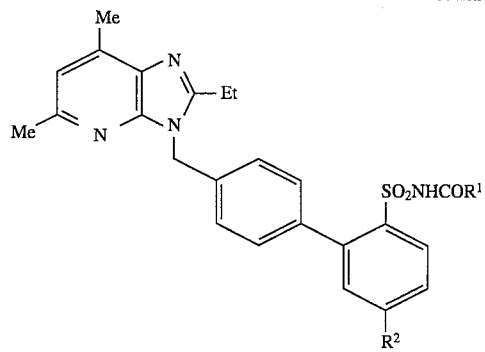

| EXAMPLE | R¹ | R² |
| --- | --- | --- |
| 6 | (CH₂)₄CH₃ | CH₂N(CH₃)₂ |
| 7 | NHn-Bu | O-n-Bu |
| 8 | (CH₂)₄CH₃ | CH(CH₃)₂ |
| 9 | CH₂OEt | (CH₂)₂CH₃ |
| 10 | CH₂On-Bu | (CH₂)₂CH₃ |
| 11 | (CH₂)₄CH₃ | CH₂N(CH₂CH₂)₂ |
| 12 | (CH₂)₄CH₃ | CH₂N(CH₂CH₂)₂O |
| 13 | (CH₂)₄CH₃ | O-n-Bu |

EXAMPLE 6

5,7-dimethyl-2-ethyl-3[[2'-(N-n-pentylcarbonylsulfonamido)-5'-dimethylaminomethyl[1,1'biphenyl]-4-yl]methylimidazo[4,5-b]pyridine (Compound 15 of Table 1)

The titled compound was prepared as follows: Intermediate 2 of scheme I ($R^2=CH_2N(CH_3)_2$) was prepared using the method described in scheme II D. Completion of the antagonist was carried out as illustrated in scheme I. The final step, preparation of compound 7 of scheme I ($R^1=(CH_2)_4CH_3$, $R^2=CH_2N(CH_3)_2$) from the free sulfonamide, was carried out using hexanoic acid and CDI (method A of scheme I).

$^1$H NMR (400 MHz, CD$_3$OD) δ 0.81 (t, 3H), 1.08 (m, 2H), 1.18 (m, 2H), 1.31 (m, 2H), 1.34 (t, 3H), 1.78 (t, 2H), 2.49 (s, 6H), 2.58 (s, 3H), 2.61 (s, 3H), 2.91 (q, 2H), 3.84 (s, 2H), 5.59 (s, 2H), 7.01 (s, 1H), 7.12 (d, 2H), 7.23 (d, 1H), 7.32 (d, 2H), 7.48 (dd, 1H), 8.12 (d, 1H).

EXAMPLE 7

5,7-dimethyl-2-ethyl-3[[2'-(N-n-butylaminocarbonylsulfonamido)-5'-n-butoxy[1,1'biphenyl]-4-yl]methylimidazo[4,5-b]pyridine (Compound 66 of Table 1)

The titled compound was prepared as follows: Intermediate 2 of scheme I ($R^2=O(CH_2)_3CH_3$) was prepared from commercailly available 4-butoxybenzenesulfonyl chloride. Completion of the antagonist was carried out as illustrated in scheme I. The final step, preparation of compound 7 of scheme I ($R^1=NH(CH_2)_3CH_3$, $R^2=O(CH_2)_3CH_3$) from the free sulfonamide, was carried out using n-butylisocyanate and DBU as base (method C of scheme I).

$^1$H NMR (400 MHz, CD$_3$OD) δ 0.81 (t, 3H), 0.96 (t, 3H), 1.13 (m, 2H), 1.23 (m, 2H), 1.33 (t, 3H), 1.47 (m, 2H), 1.75 (m, 2H), 2.58 (s, 3H), 2.61 (s, 3H), 2.91 (q, 4H), 4.03 (t, 2H), 5.60 (s, 2H), 6.73 (d, 1H), 7.01 (s, 1H), 7.02 (dd, 1H), 7.13 (d, 2H), 7.28 (d, 2H), 8.03 (d, 1H).

EXAMPLE 8

5,7-dimethyl-2-ethyl-3[[2'-(N-n-pentylcarbonylsulfonamido)-5'-isopropyl[1,1'biphenyl]-4-yl]methylimidazo[4,5-b]pyridine (Compound 5 of Table 1)

The titled compound was prepared as follows: Intermediate 2 of scheme I ($R^2=CH(CH_3)_2$) was prepared from commercially available 4-butoxybenzenesulfonyl chloride. Completion of the antagonist was carried out as illustrated in scheme I. The final step, preparation of compound 7 of scheme I ($R^1=(CH_2)_4CH_3$, $R^2=CH(CH_3)_2$) from the free sulfonamide, was carried out using hexanoic acid and CDI (method A of scheme I).

$^1$H NMR (400 MHz, CD$_3$OD) δ 0.79 (t, 3H), 1.05 (m, 2H), 1.17 (m, 2H), 1.24 (d, 6H), 1.33 (t, 3H), 1.34 (m, 2H), 1.79 (t, 2H), 2.57 (s, 3H), 2.61 (s, 3H), 2.91 (m, 3H), 5.61 (s, 2H), 7.01 (s, 1H), 7.08 (d, 1H), 7.13 (d, 2H), 7.28 (d, 2H), 7.40 (dd, 1H), 8.07 (d, 1H).

EXAMPLE 9

5,7-dimethyl-2-ethyl-3[[2'-(N-ethoxymethylcarbonylsulfonamido)-5'-n-propyl[1,1'biphenyl]-4-yl]methylimidazo[4,5-b]pyridine (Compound 43 of Table 1)

The titled compound was prepared from the product of Example 1, step D. Completion of the antagonist was carried out as illustrated in scheme I. The final step, preparation of compound 7 of scheme I ($R^1=CH_2OCH_2CH_3$, $R^2=(CH_2)_2CH_3$) from the free sulfonamide, was carried out using ethoxyacetic acid and CDI (method A of scheme I).

$^1$H NMR (400 MHz, CD$_3$OD) δ 0.93 (t, 3H), 1.04 (t, 3H), 1.35 (t, 3H), 1.62 (m, 2H), 2.58 (s, 3H), 2.60 (s, 3H), 2.61 (t, 2H), 2.91 (q, 2H), 3.28 (t, 2H), 3.45 (s, 2H), 5.59 (s, 2H), 6.99 (d, 1H), 7.01 (s, 1H), 7.11 (d, 2H), 7.28 (dd, 1H), 7.33 (d, 2H), 8.02 (d, 1H).

EXAMPLE 10

5,7-dimethyl-2-ethyl-3[[2'-(N-(n-butoxy)methylcarbonylsulfonamido)-5'-n-propyl[1,1'biphenyl]-4-yl]methylimidazo[4,5-b]pyridine (Compound 23 of Table 1)

The titled compound was prepared from the product of Example 1, step D. Completion of the antagonist was carried out as illustrated in scheme I. The final step, preparation of compound 7 of scheme I ($R^1=CH_2O(CH_2)_3CH_3$, $R^2=(CH_2)_2CH_3$) from the free sulfonamide, was carried out using n-butoxyacetic acid and CDI (method A of scheme I).

$^1$H NMR (400 MHz, CD$_3$OD) δ 0.84 (t, 3H), 0.93 (t, 3H), 1.22 (m, 2H), 1.35 (t, 3H), 1.39 (m, 2H), 1.62 (m, 2H), 2.58 (s, 3H), 2.61 (s, 3H), 2.62 (t, 2H), 2.91 (q, 2H), 3.21 (t, 2H), 3.43 (s, 2H), 5.59 (s, 2H), 6.99 (d, 1H), 7.01 (s, 1H), 7.11 (d, 2H), 7.28 (dd, 1H), 7.32 (d, 2H), 8.03 (d, 1H).

EXAMPLE 11

5,7-dimethyl-2-ethyl-3[[2'-(N-n-pentylcarbonylsulfonamido)-5'-pyrrolidin-1-ylmethyl[1,1'biphenyl]-4-yl]methylimidazo[4,5-b]pyridine (Compound 16 of Table 1)

The titled compound was prepared as follows: Intermediate 2 of scheme I ($R^2=CH_2N(CH_2CH_2)_2$) was prepared using the method described in scheme II D. Completion of the antagonist was carried out as illustrated in scheme I. The final step, preparation of compound 7 of scheme I ($R^1=(CH_2)_4CH_3$, $R^2=CH_2N(CH_2CH_2)_2$) from the free sulfonamide, was carried out using hexanoic acid and CDI (method A of scheme I).

$^1$H NMR (400 MHz, CD$_3$OD) δ 0.81 (t, 3H), 1.11 (m, 2H), 1.19 (m, 2H), 1.32 (m, 5H), 1.79 (t, 2H), 1.98 (bs, 4H), 2.57 (s, 3H), 2.60 (s, 3H), 2.91 (q, 2H), 3.12 (bs, 4H), 4.21 (s, 2H), 5.59 (s, 2H), 6.99 (s, 1H), 7.11 (d, 2H), 7.28 (d, 1H), 7.31 (d, 2H), 7.51 (dd, 1H), 8.10 (d, 1H).

EXAMPLE 12

5,7-dimethyl-2-ethyl-3[[2'-(N-n-pentylcarbonylsulfonamido)-5'-morpholin-1-ylmethyl[1,1'biphenyl]-4-yl]methylimidazo[4,5-b]pyridine (Compound 17 of Table 1)

The titled compound was prepared as follows: Intermediate 2 of scheme I ($R^2=CH_2N(CH_2CH_2)_2O$) was prepared using the method o described in scheme II D. Completion of the antagonist was carried out as illustrated in scheme I. The final step, preparation of compound 7 of scheme I ($R^1$= $(CH_2)_4CH_3$, $R_2$=$CH_2N(CH_2CH_2)_2O$) from the free sulfonamide, was carried out using hexanoic acid and CDI (method A of scheme I).

$^1$H NMR (400 MHz, $CD_3OH$) δ0.80 (t, 3H), 1.04 (m, 2H), 1.15 (m, 2H), 1.31–1.39 (m, 5H), 1.80 (t, 2H), 2.50 (bs, 4H) 2.58 (s, 3H), 2.62 (s, 3H), 2.92 (q, 2H), 3.62 (bs 2H), 3.68 (bm, 4H), 5.61 (s, 2H), 7.04 (s, 1H), 7.1 (d, 2H), 7.26 (s, 1H), 7.27 (d, 2H), 7.56 (dd, 1H) 8.12 ( d, 1H).

EXAMPLE 13

5,7-dimethyl-2-ethyl-3[[2'-(N-n-pentylcarbonylsulfonamido)-5'-n-butoxy[1,1'biphenyl]-4-yl]methylimidazo[4,5-b]pyridine (Compound 6 of Table 1)

The titled compound was prepared as follows: Intermediate 2 of scheme I ($R^2$=$O(CH_2)_3CH_3$) was prepared from commercially available 4-butoxybenzenesulfonyl chloride. Completion of the antagonist was carried out as illustrated in scheme I. The final step, preparation of compound 7 of scheme I ($R^1$=$(CH_2)_4CH_3$, $R^2$=$O(CH_2)_3CH_3$) from the free sulfonamide, was carried out using hexanoic acid and CDI (method A of scheme I).

$^1$H NMR (400 MHz, $CD_3OD$) δ 0.80 (t, 3H), 0.96 (t, 3H ), 1.07 (m, 2H), 1.17 (m. 2H), 1.32 (m, 2H), 1.35 (t, 3H), 1.49 (m, 2H), 1.75 (m, 2H), 1.83 (t, 2H), 2.58 (s, 3H), 2.61 (s, 3H), 2.92 (q, 4H), 4.04 (t, 2H), 5.61 (s, 2H), 6.73 (d. 1H), 7.02 (s, 1H), 7.04 (dd, 1H), 7.13 (d, 2H), 7.28 (d, 2H), 8.09 (d, 1H).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per Capsule (mg) |
| --- | --- |
| Compound 1 | 50 |
| Lactose | 149 |
| Magnesium stearate | 1 |
| Capsule (size No. 1) | 200 |

Compound 1 can be reduces to a No. 60 powder and the lactose and magnesium stearate can then be passed through a No. 60 blotting cloth onto the powder. The combined ingreidents can then be mixed for about 10 minutes and fikkes into a No. 1 dry gelatin capsule.

B: Tablet

A typical tablet would contain Compound 1 (25 mg), pregelatinized starch USP (82 mg), microcrystaline cellulose (82 mg) and magnesium stearate (1 mg).

C: Combination Tablet

A typical suppository formulations for rectal administration can contain Compound 1 (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium clacium edetate and a hydrogenated vegetable oil (675–1400 mg) such as Suppocire L, Wecobee FS, Wecobee M, Witepsols, and the like, for the polyethylene glucol. Further, these suppository formulations can also include another active ingreidnet such as another antihypertensive and/or a diuretic and/or an angiotensin converting enzyme and/or a calcium channel blocker in pharmaceutically effective amounts as described, for example, in C above.

E: Infection

A typical injectable formulation would contain Compound 1 (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertansive and/or a diuretic and/or an angiotensin converting enzyme inhibitor and/or a calcium channel blocker.

What is claimed is:

1. A compound of structural formula:

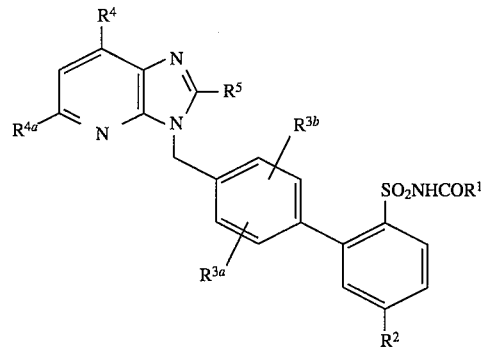

or a pharmaceutically acceptable salt thereof, wherein
$R^1$ is
  a) $C_{1-6}$ alkyl,
  b) $C_{1-6}$ alkylamino,
  c) $C_{1-6}$ alkoxy-$(CH_2)_n$—, wherein n is 1 or 2,
  d) aryl $S(O)_q$—, wherein q is 0 to 3,
  e) $C_{1-6}$ alkylthio-$(CH_2)_n$—,
  f) aryl, either unsubstituted or substituted with
    1) $C_{1-6}$ alkyl,
    2) aryloxy,
    3) $C_{1-6}$ alkoxy,
    4) —Cl,
    5) —Br, or
    6) $C_{1-6}$ alkylamino;
$R^2$ is
  a) —Cl,
  b) $C_{1-6}$ alkyl,
  c) $C_{1-5}$ alkoxy,
  d) $C_{1-5}$ alkoxy-$CH_2$—,
  e) di($C_{1-5}$ alkyl) amino-$CH_2$—,
  f) pyrrolidin-1-yl-$CH_2$—,
  g) morpholin-1-yl-$CH_2$—,
  h) polyfluoro-$C_{1-5}$ alkoxy,
  i) aryl,
  j) $C_{1-5}$ alkyl $S(O)_q$-$(CH_2)_q$,
  k) aryl-$(CH_2)_n$—;
$R^{3a}$ and $R^{3b}$ are independently
  a) H,
  b) F, Cl, Br or I,
  c) $C_{1-4}$ alkyl,
  d) $C_{1-4}$ alkyoxy, or
  e) aryl;
$R^{3a}$ and $R^{3b}$ on adjacent carbons can be joined together to form a benzo group;

$R^4$ and $R^{4a}$ are independently
  a) $C_{1-3}$ alkyl,
  b) polyfluoro-$C_{1-3}$ alkyl,
  c) —COHNR$^1$,
  d) —CO$_2$R$^1$ or
  e) —CONH(CH$_2$)$_n$-aryl; and
$R^5$ is hydrogen or $C_{1-5}$ alkyl, 2. The compound of claim 1, or a pharmaceutically acceptable salt thereof, wherein $R^4$ and $R^{4a}$ are both $C_{1-3}$ alkyl, and $R^5$ is $C_{1-5}$ alkyl.

3. The compound of claim 2, or a pharmaceutically acceptable salt thereof, wherein $R^4$ and $R^{4a}$ are both methyl and $R^5$ is ethyl.

4. The compound of claim 3, or a pharmaceutically acceptable salt thereof selected from the group consisting those in the following list:

TABLE 3

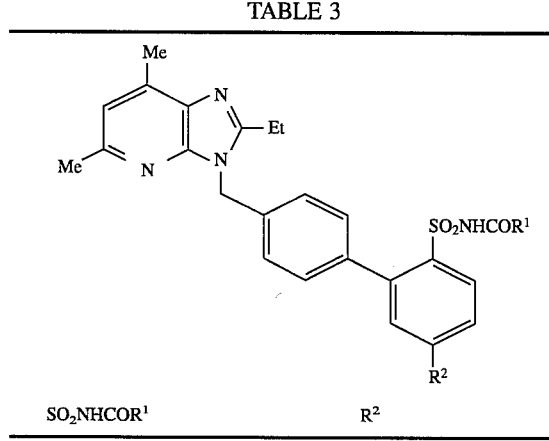

| SO$_2$NHCOR$^1$ | R$^2$ |
|---|---|
| SO$_2$NHCO(CH$_2$)$_4$CH$_3$ | CH$_3$ |
| SO$_2$NHCO(CH$_2$)$_4$CH$_3$ | CH$_2$CH$_3$ |
| SO$_2$NHCO(CH$_2$)$_4$CH$_3$ | (CH$_2$)$_2$CH$_3$ |
| SO$_2$NHCO(CH$_2$)$_4$CH$_3$ | (CH$_2$)$_3$CH$_3$ |
| SO$_2$NHCO(CH$_2$)$_4$CH$_3$ | CH(CH$_3$)$_2$ |
| SO$_2$NHCO(CH$_2$)$_4$CH$_3$ | O(CH$_2$)$_3$CH$_3$ |
| SO$_2$NHCO(CH$_2$)$_4$CH$_3$ | CH$_2$CH(CH$_3$)$_2$ |
| SO$_2$NHCO(CH$_2$)$_4$CH$_3$ | OCH$_3$ |
| SO$_2$NHCO(CH$_2$)$_4$CH$_3$ | CH$_2$SCH$_3$ |
| SO$_2$NHCO(CH$_2$)$_4$CH$_3$ | CH$_2$OCH$_3$ |
| SO$_2$NHCO(CH$_2$)$_4$CH$_3$ | OCH$_2$CH$_3$ |
| SO$_2$NHCO(CH$_2$)$_4$CH$_3$ | Ph |
| SO$_2$NHCO(CH$_2$)$_4$CH$_3$ | C(CH$_3$)$_2$CH$_2$CH$_3$ |
| SO$_2$NHCO(CH$_2$)$_4$CH$_3$ | C(CH$_3$)$_3$ |
| SO$_2$NHCO(CH$_2$)$_4$CH$_3$ | CH$_2$N(CH$_3$)$_2$ |
| SO$_2$NHCO(CH$_2$)$_4$CH$_3$ | CH$_2$N(CH$_2$CH$_2$)$_2$ |
| SO$_2$NHCO(CH$_2$)$_4$CH$_3$ | CH$_2$N(CH$_2$CH$_2$)$_2$O |
| SO$_2$NHCO(CH$_2$)$_4$CH$_3$ | OCH$_2$CF$_3$ |
| SO$_2$NHCO(CH$_2$)$_4$CH$_3$ | OCH(CH$_3$)$_2$ |
| SO$_2$NHCO(CH$_2$)$_4$CH$_3$ | SCH$_2$CH$_3$ |
| SO$_2$NHCOCH$_2$O(CH$_2$)$_3$CH$_3$ | CH$_3$ |
| SO$_2$NHCOCH$_2$O(CH$_2$)$_3$CH$_3$ | CH$_2$CH$_3$ |
| SO$_2$NHCOCH$_2$O(CH$_2$)$_3$CH$_3$ | (CH$_2$)$_2$CH$_3$ |
| SO$_2$NHCOCH$_2$O(CH$_2$)$_3$CH$_3$ | (CH$_2$)$_3$CH$_3$ |
| SO$_2$NHCOCH$_2$O(CH$_2$)$_3$CH$_3$ | CH(CH$_3$)$_2$ |
| SO$_2$NHCOCH$_2$O(CH$_2$)$_3$CH$_3$ | O(CH$_2$)$_3$CH$_3$ |
| SO$_2$NHCOCH$_2$O(CH$_2$)$_3$CH$_3$ | CH$_2$CH(CH$_3$)$_2$ |
| SO$_2$NHCOCH$_2$O(CH$_2$)$_3$CH$_3$ | OCH$_3$ |
| SO$_2$NHCOCH$_2$O(CH$_2$)$_3$CH$_3$ | CH$_2$SCH$_3$ |
| SO$_2$NHCOCH$_2$O(CH$_2$)$_3$CH$_3$ | CH$_2$OCH$_3$ |
| SO$_2$NHCOCH$_2$O(CH$_2$)$_3$CH$_3$ | OCH$_2$CH$_3$ |
| SO$_2$NHCOCH$_2$O(CH$_2$)$_3$CH$_3$ | Ph |
| SO$_2$NHCOCH$_2$O(CH$_2$)$_3$CH$_3$ | C(CH$_3$)$_2$CH$_2$CH$_3$ |
| SO$_2$NHCOCH$_2$O(CH$_2$)$_3$CH$_3$ | C(CH$_3$)$_3$ |
| SO$_2$NHCOCH$_2$O(CH$_2$)$_3$CH$_3$ | CH$_2$N(CH$_3$)$_2$ |
| SO$_2$NHCOCH$_2$O(CH$_2$)$_3$CH$_3$ | CH$_2$N(CH$_2$CH$_2$)$_2$ |
| SO$_2$NHCOCH$_2$O(CH$_2$)$_3$CH$_3$ | CH$_2$N(CH$_2$CH$_2$)$_2$O |
| SO$_2$NHCOCH$_2$O(CH$_2$)$_3$CH$_3$ | OCH$_2$CF$_3$ |
| SO$_2$NHCOCH$_2$O(CH$_2$)$_3$CH$_3$ | OCH(CH$_3$)$_2$ |

TABLE 3-continued

| SO$_2$NHCOR$^1$ | R$^2$ |
|---|---|
| SO$_2$NHCOCH$_2$O(CH$_2$)$_3$CH$_3$ | SCH$_2$CH$_3$ |
| SO$_2$NHCOCH$_2$OCH$_2$CH$_3$ | CH$_3$ |
| SO$_2$NHCOCH$_2$OCH$_2$CH$_3$ | CH$_2$CH$_3$ |
| SO$_2$NHCOCH$_2$OCH$_2$CH$_3$ | (CH$_2$)$_2$CH$_3$ |
| SO$_2$NHCOCH$_2$OCH$_2$CH$_3$ | (CH$_2$)$_3$CH$_3$ |
| SO$_2$NHCOCH$_2$OCH$_2$CH$_3$ | CH(CH$_3$)$_2$ |
| SO$_2$NHCOCH$_2$OCH$_2$CH$_3$ | O(CH$_2$)$_3$CH$_3$ |
| SO$_2$NHCOCH$_2$OCH$_2$CH$_3$ | CH$_2$CH(CH$_3$)$_2$ |
| SO$_2$NHCOCH$_2$OCH$_2$CH$_3$ | OCH$_3$ |
| SO$_2$NHCOCH$_2$OCH$_2$CH$_3$ | CH$_2$SCH$_3$ |
| SO$_2$NHCOCH$_2$OCH$_2$CH$_3$ | CH$_2$OCH$_3$ |
| SO$_2$NHCOCH$_2$OCH$_2$CH$_3$ | OCH$_2$CH$_3$ |
| SO$_2$NHCOCH$_2$OCH$_2$CH$_3$ | Ph |
| SO$_2$NHCOCH$_2$OCH$_2$CH$_3$ | C(CH$_3$)$_2$CH$_2$CH$_3$ |
| SO$_2$NHCOCH$_2$OCH$_2$CH$_3$ | C(CH$_3$)$_3$ |
| SO$_2$NHCOCH$_2$OCH$_2$CH$_3$ | CH$_2$N(CH$_3$)$_2$ |
| SO$_2$NHCOCH$_2$OCH$_2$CH$_3$ | CH$_2$N(CH$_2$CH$_2$)$_2$ |
| SO$_2$NHCOCH$_2$OCH$_2$CH$_3$ | CH$_2$N(CH$_2$CH$_2$)$_2$O |
| SO$_2$NHCOCH$_2$OCH$_2$CH$_3$ | OCH$_2$CF$_3$ |
| SO$_2$NHCOCH$_2$OCH$_2$CH$_3$ | OCH(CH$_3$)$_2$ |
| SO$_2$NHCONH(CH$_2$)$_3$CH$_3$ | SCH$_2$CH$_3$ |
| SO$_2$NHCONH(CH$_2$)$_3$CH$_3$ | CH$_3$ |
| SO$_2$NHCONH(CH$_2$)$_3$CH$_3$ | CH$_2$CH$_3$ |
| SO$_2$NHCONH(CH$_2$)$_3$CH$_3$ | (CH$_2$)$_2$CH$_3$ |
| SO$_2$NHCONH(CH$_2$)$_3$CH$_3$ | (CH$_2$)$_3$CH$_3$ |
| SO$_2$NHCONH(CH$_2$)$_3$CH$_3$ | CH(CH$_3$)$_2$ |
| SO$_2$NHCONH(CH$_2$)$_3$CH$_3$ | O(CH$_2$)$_3$CH$_3$ |
| SO$_2$NHCONH(CH$_2$)$_3$CH$_3$ | CH$_2$CH(CH$_3$)$_2$ |
| SO$_2$NHCONH(CH$_2$)$_3$CH$_3$ | OCH$_3$ |
| SO$_2$NHCONH(CH$_2$)$_3$CH$_3$ | CH$_2$SCH$_3$ |
| SO$_2$NHCONH(CH$_2$)$_3$CH$_3$ | CH$_2$OCH$_3$ |
| SO$_2$NHCONH(CH$_2$)$_3$CH$_3$ | OCH$_2$CH$_3$ |
| SO$_2$NHCONH(CH$_2$)$_3$CH$_3$ | Ph |
| SO$_2$NHCONH(CH$_2$)$_3$CH$_3$ | C(CH$_3$)$_2$CH$_2$CH$_3$ |
| SO$_2$NHCONH(CH$_2$)$_3$CH$_3$ | C(CH$_3$)$_3$ |
| SO$_2$NHCONH(CH$_2$)$_3$CH$_3$ | CH$_2$N(CH$_3$)$_2$ |
| SO$_2$NHCONH(CH$_2$)$_3$CH$_3$ | CH$_2$N(CH$_2$CH$_2$)$_2$ |
| SO$_2$NHCONH(CH$_2$)$_3$CH$_3$ | CH$_2$N(CH$_2$CH$_2$)$_2$O |
| SO$_2$NHCONH(CH$_2$)$_3$CH$_3$ | OCH$_2$CF$_3$ |
| SO$_2$NHCONH(CH$_2$)$_3$CH$_3$ | OCH(CH$_3$)$_2$ |
| SO$_2$NHCONH(CH$_2$)$_3$CH$_3$ | SCH$_2$CH$_3$ |
| SO$_2$NHCO(CH$_2$)$_2$Ph | CH$_3$ |
| SO$_2$NHCO(CH$_2$)$_2$Ph | CH$_2$CH$_3$ |
| SO$_2$NHCO(CH$_2$)$_2$Ph | (CH$_2$)$_2$CH$_3$ |
| SO$_2$NHCO(CH$_2$)$_2$Ph | (CH$_2$)$_3$CH$_3$ |
| SO$_2$NHCO(CH$_2$)$_2$Ph | CH(CH$_3$)$_2$ |
| SO$_2$NHCO(CH$_2$)$_2$Ph | O(CH$_2$)$_3$CH$_3$ |
| SO$_2$NHCO(CH$_2$)$_2$Ph | CH$_2$CH(CH$_3$)$_2$ |
| SO$_2$NHCO(CH$_2$)$_2$Ph | OCH$_3$ |
| SO$_2$NHCO(CH$_2$)$_2$Ph | CH$_2$SCH$_3$ |
| SO$_2$NHCO(CH$_2$)$_2$Ph | CH$_2$OCH$_3$ |
| SO$_2$NHCO(CH$_2$)$_2$Ph | OCH$_2$CH$_3$ |
| SO$_2$NHCO(CH$_2$)$_2$Ph | Ph |
| SO$_2$NHCO(CH$_2$)$_2$Ph | C(CH$_3$)$_2$CH$_2$CH$_3$ |
| SO$_2$NHCO(CH$_2$)$_2$Ph | C(CH$_3$)$_3$ |
| SO$_2$NHCO(CH$_2$)$_2$Ph | CH$_2$N(CH$_3$)$_2$ |
| SO$_2$NHCO(CH$_2$)$_2$Ph | CH$_2$N(CH$_2$CH$_2$)$_2$ |
| SO$_2$NHCO(CH$_2$)$_2$Ph | CH$_2$N(CH$_2$CH$_2$)$_2$O |
| SO$_2$NHCO(CH$_2$)$_2$Ph | OCH$_2$CF$_3$ |

TABLE 3-continued

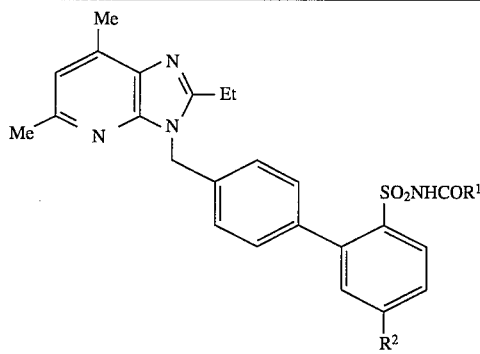

| SO$_2$NHCOR$^1$ | R$^2$ |
|---|---|
| SO$_2$NHCO(CH$_2$)$_2$Ph | OCH(CH$_3$)$_2$ |
| SO$_2$NHCO(CH$_2$)$_2$Ph | SCH$_2$CH$_3$ |
| SO$_2$NHCO(2-PhO)Ph | CH$_3$ |
| SO$_2$NHCO(2-PhO)Ph | CH$_2$CH$_3$ |
| SO$_2$NHCO(2-PhO)Ph | (CH$_2$)$_2$CH$_3$ |
| SO$_2$NHCO(2-PhO)Ph | CH(CH$_3$)$_2$ |
| SO$_2$NHCO(2-PhO)Ph | O(CH$_2$)$_3$CH$_3$ |
| SO$_2$NHCO(2-PhO)Ph | CH$_2$CH(CH$_3$)$_2$ |
| SO$_2$NHCO(2-PhO)Ph | OCH$_3$ |
| SO$_2$NHCO(2-PhO)Ph | CH$_2$SCH$_3$ |
| SO$_2$NHCO(2-PhO)Ph | CH$_2$OCH$_3$ |
| SO$_2$NHCO(2-PhO)Ph | OCH$_2$CH$_3$ |
| SO$_2$NHCO(2-PhO)Ph | Ph |
| SO$_2$NHCO(2-PhO)Ph | C(CH$_3$)$_2$CH$_2$CH$_3$ |
| SO$_2$NHCO(2-PhO)Ph | C(CH$_3$)$_3$ |
| SO$_2$NHCO(2-PhO)Ph | CH$_2$N(CH$_3$)$_2$ |
| SO$_2$NHCO(2-PhO)Ph | CH$_2$N(CH$_2$CH$_2$)$_2$ |
| SO$_2$NHCO(2-PhO)Ph | CH$_2$N(CH$_2$CH$_2$)$_2$O |
| SO$_2$NHCO(2-PhO)Ph | OCH$_2$CF$_3$ |
| SO$_2$NHCO(2-PhO)Ph | OCH(CH$_3$)$_2$ |
| SO$_2$NHCO(2-PhO)Ph | SCH$_2$CH$_3$ |
| SO$_2$NHCO(2-EtO)Ph | CH$_3$ |
| SO$_2$NHCO(2-EtO)Ph | CH$_2$CH$_3$ |
| SO$_2$NHCO(2-EtO)Ph | (CH$_2$)$_2$CH$_3$ |
| SO$_2$NHCO(2-EtO)Ph | CH(CH$_3$)$_2$ |
| SO$_2$NHCO(2-EtO)Ph | O(CH$_2$)$_3$CH$_3$ |
| SO$_2$NHCO(2-EtO)Ph | CH$_2$CH(CH$_3$)$_2$ |
| SO$_2$NHCO(2-EtO)Ph | OCH$_3$ |
| SO$_2$NHCO(2-EtO)Ph | CH$_2$SCH$_3$ |
| SO$_2$NHCO(2-EtO)Ph | CH$_2$OCH$_3$ |
| SO$_2$NHCO(2-EtO)Ph | OCH$_2$CH$_3$ |
| SO$_2$NHCO(2-EtO)Ph | Ph |
| SO$_2$NHCO(2-EtO)Ph | C(CH$_3$)$_2$CH$_2$CH$_3$ |
| SO$_2$NHCO(2-EtO)Ph | C(CH$_3$)$_3$ |
| SO$_2$NHCO(2-EtO)Ph | CH$_2$N(CH$_3$)$_2$ |
| SO$_2$NHCO(2-EtO)Ph | CH$_2$N(CH$_2$CH$_2$)$_2$ |
| SO$_2$NHCO(2-EtO)Ph | CH$_2$N(CH$_2$CH$_2$)$_2$O |
| SO$_2$NHCO(2-EtO)Ph | OCH$_2$CF$_3$ |
| SO$_2$NHCO(2-EtO)Ph | OCH(CH$_3$)$_2$ |
| SO$_2$NHCO(2-EtO)Ph | SCH$_2$CH$_3$ |
| SO$_2$NHCOPh | CH$_3$ |
| SO$_2$NHCOPh | CH$_2$CH$_3$ |
| SO$_2$NHCOPh | (CH$_2$)$_2$CH$_3$ |
| SO$_2$NHCOPh | CH(CH$_3$)$_2$ |
| SO$_2$NHCOPh | O(CH$_2$)$_3$CH$_3$ |
| SO$_2$NHCOPh | CH$_2$N(CH$_3$)$_2$ |
| SO$_2$NHCOPh | OCH$_3$ |
| SO$_2$NHCOPh | CH$_2$SCH$_3$ |
| SO$_2$NHCOPh | CH$_2$OCH$_3$ |
| SO$_2$NHCOPh | OCH$_2$CH$_3$ |
| SO$_2$NHCOPh | Ph |
| SO$_2$NHCOPh | C(CH$_3$)$_2$CH$_2$CH$_3$ |
| SO$_2$NHCOPh | C(CH$_3$)$_3$ |
| SO$_2$NHCOPh | CH$_2$N(CH$_3$)$_2$ |
| SO$_2$NHCOPh | CH$_2$N(CH$_2$CH$_2$)$_2$ |
| SO$_2$NHCOPh | CH$_2$N(CH$_2$CH$_2$)$_2$O |
| SO$_2$NHCOPh | OCH$_2$CF$_3$ |
| SO$_2$NHCOPh | OCH(CH$_3$)$_2$ |
| SO$_2$NHCOPh | SCH$_2$CH$_3$ |
| SO$_2$NHCOCH$_2$O(CH$_2$)$_2$CH$_3$ | CH$_3$ |

TABLE 3-continued

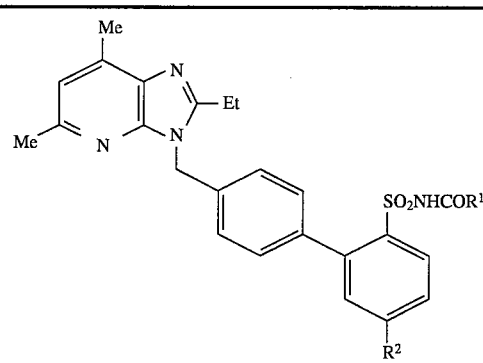

| SO$_2$NHCOR$^1$ | R$^2$ |
|---|---|
| SO$_2$NHCOCH$_2$O(CH$_2$)$_2$CH$_3$ | CH$_2$CH$_3$ |
| SO$_2$NHCOCH$_2$O(CH$_2$)$_2$CH$_3$ | (CH$_2$)$_2$CH$_3$ |
| SO$_2$NHCOCH$_2$O(CH$_2$)$_2$CH$_3$ | CH(CH$_3$)$_2$ |
| SO$_2$NHCOCH$_2$O(CH$_2$)$_2$CH$_3$ | O(CH$_2$)$_3$CH$_3$ |
| SO$_2$NHCOCH$_2$O(CH$_2$)$_2$CH$_3$ | OCH$_3$ |
| SO$_2$NHCOCH$_2$O(CH$_2$)$_2$CH$_3$ | CH$_2$SCH$_3$ |
| SO$_2$NHCOCH$_2$O(CH$_2$)$_2$CH$_3$ | CH$_2$OCH$_3$ |
| SO$_2$NHCOCH$_2$O(CH$_2$)$_2$CH$_3$ | OCH$_2$CH$_3$ |
| SO$_2$NHCOCH$_2$O(CH$_2$)$_2$CH$_3$ | Ph |
| SO$_2$NHCOCH$_2$O(CH$_2$)$_2$CH$_3$ | C(CH$_3$)$_2$CH$_2$CH$_3$ |
| SO$_2$NHCOCH$_2$O(CH$_2$)$_2$CH$_3$ | C(CH$_3$)$_3$ |
| SO$_2$NHCOCH$_2$O(CH$_2$)$_2$CH$_3$ | CH$_2$N(CH$_3$)$_2$ |
| SO$_2$NHCOCH$_2$O(CH$_2$)$_2$CH$_3$ | CH$_2$N(CH$_2$CH$_2$)$_2$ |
| SO$_2$NHCOCH$_2$O(CH$_2$)$_2$CH$_3$ | CH$_2$N(CH$_2$CH$_2$)$_2$O |
| SO$_2$NHCOCH$_2$O(CH$_2$)$_2$CH$_3$ | OCH$_2$CF$_3$ |
| SO$_2$NHCOCH$_2$O(CH$_2$)$_2$CH$_3$ | OCH(CH$_3$)$_2$ |
| SO$_2$NHCOCH$_2$O(CH$_2$)$_2$CH$_3$ | SCH$_2$CH$_3$. |

5. The compound of claim 4 or a pharmaceutically acceptable salt thereof selected from the group consisting of:

5,7-dimethyl-2-ethyl-3[[2'-(N-n-pentylcarbonylsulfonamido)-5'-n-propyl[1,1'biphenyl]-4-yl]methylimidazo[4,5-b]pyridine;

5,7-dimethyl-2-ethyl-3[[2'-(N-n-butylaminocarbonylsulfonamido)-5'-n-propyl-[1,1'biphenyl]-4-yl]methylimidazo[4,5-b]pyridine;

5,7-dimethyl-2-ethyl-3[[2'-(N-(2-phenylethyl)carbonylsulfonamido)-5'-n-propyl[1,1'biphenyl]-4-yl]methylimidazo[4,5-b]pyridine;

5,7-dimethyl-2-ethyl-3[[2'-(N-(2-phenoxyphenyl)carbonylsulfonamido)-5'-n-propyl[1,1'biphenyl]-4-yl]methylimidazo[4,5-b]pyridine;

5,7-dimethyl-2-ethyl-3[[2'-(N-benzenecarbonylsulfonamido)-5'-n-propyl[1,1'biphenyl]-4-yl]methylimidazo[4,5-b]pyridine;

5,7-dimethyl-2-ethyl-3[[2'-(N-n-pentylcarbonylsulfonamido)-5'-dimethylaminomethyl[1,1'biphenyl]-4-yl]methylimidazo[4,5-b]pyridine;

5,7-dimethyl-2-ethyl-3[[2'-(N-n-butylaminocarbonylsulfonamido)-5'-n-butoxy[1,1'biphenyl]-4-yl]methylimidazo[4,5-b]pyridine;

5,7-dimethyl-2-ethyl-3[[2'-(N-n-pentylcarbonylsulfonamido)-5'-isopropyl[1,1'biphenyl]-4-yl]methylimidazo4,5-b]pyridine;

5,7-dimethyl-2-ethyl-3[[2'-(N-ethoxymethylcarbonylsulfonamido)-5'-n-propyl[1,1'biphenyl]-4-yl]methylimidazo[4,5-b]pyridine;

5,7-dimethyl-2-ethyl-3[[2'-(N-(n-butoxy)methylcarbonylsulfonamido)-5'-n-propyl[1,1'biphenyl]-4-yl]methylimidazo[4,5-b]pyridine;

5,7-dimethyl-2-ethyl-3[[2'-(N-n-pentylcarbonylsulfonamido)-5'-pyrrolidin-1-ylmethyl[1,1'biphenyl]-4-yl]methylimidazo[4,5-b]pyridine;

5,7-dimethyl-2-ethyl-3[[2'-(N-n-pentylcarbonylsulfonamido)-5'-morpholin-1-ylmethyl[1,1'biphenyl]-4-yl] methylimidazo[4,5-b]pyridine; and 5,7-dimethyl-2-ethyl-3[[2'-(N-n-pentylcarbonylsulfonamido)-5'-n-butoxy[1,1'biphenyl]-4-yl]methylimidazo [4,5-b]pyridine.

6. A pharmaceutical composition useful in the treatment of hypertension which comprises a pharmaceutically acceptable carrier and a pharmaceutically effective amount of a compound of claim 1 or a pharmaceutically acceptable salt thereof.

7. A method of treating hypertension which comprises administering to a patient in need of such treatment a pharmaceutically effective amount of a compound of claim 1 or a pharmaceutically acceptable salt thereof.

8. An ophthalmological formulation for the treatment of ocular hypertension comprising an ophthalmologically acceptable carrier and an effective ocular antihypertensive amount of a compound of claim 1 or a pharmaceutically acceptable salt thereof.

9. A method of treating ocular hypertension comprising administering to a patient in need of such treatment an effective ocular antihypertensive amount of a compound of claim 1 or a pharmaceutically acceptable salt thereof.

* * * * *